United States Patent [19]

Buchecker et al.

[11] Patent Number: 5,244,597
[45] Date of Patent: Sep. 14, 1993

[54] LIQUID CRYSTALLINE MIXTURES HAVING A CHIRAL TILTED SMECTIC PHASE

[75] Inventors: Richard Buchecker, Zurich; Stephen Kelly, Möhlin; Frans Leenhouts, Kaiseraugst, all of Switzerland

[73] Assignee: Hoffmann-La Roche Inc., Nutley, N.J.

[21] Appl. No.: 898,395

[22] Filed: Jun. 11, 1992

Related U.S. Application Data

[63] Continuation of Ser. No. 346,189, May 2, 1989, abandoned.

[30] Foreign Application Priority Data

May 26, 1988 [CH] Switzerland ............ 1989/88
Apr. 5, 1989 [CH] Switzerland ............ 1248/89

[51] Int. Cl.$^5$ .................. C09K 19/30; C09K 19/34; C07D 239/02; C07D 211/72
[52] U.S. Cl. ................. 252/299.63; 252/299.01; 252/299.61; 252/299.66; 252/299.67; 359/103; 544/242; 544/298; 544/335; 546/290; 546/340; 546/346
[58] Field of Search ............ 252/299.01, 299.61, 252/299.62, 299.63, 299.66, 299.67; 359/103, 104; 544/242, 298, 335; 546/1, 340, 346, 290

[56] References Cited

U.S. PATENT DOCUMENTS

| | | | |
|---|---|---|---|
| 4,592,858 | 6/1986 | Higuchi et al. | 252/299.66 |
| 4,723,005 | 2/1988 | Huynh-Ba et al. | 252/299.63 |
| 4,753,752 | 6/1988 | Raynes et al. | 252/299.65 |
| 4,855,429 | 8/1989 | Heppke et al. | 544/355 |
| 4,867,903 | 9/1990 | Nohira et al. | 252/299.61 |
| 4,873,018 | 10/1989 | Nohira et al. | 252/299.01 |
| 4,961,876 | 10/1990 | Demus et al. | 252/299.67 |
| 5,100,577 | 3/1992 | Buchecker et al. | 252/299.01 |

FOREIGN PATENT DOCUMENTS

| | | |
|---|---|---|
| 225195 | 6/1987 | European Pat. Off. |
| 218037 | 8/1985 | United Kingdom |
| WO87/05017 | 8/1987 | World Int. Prop. O. |

OTHER PUBLICATIONS

"Some New α-Fluoro Incorporating a Cyclohexane Ring as Chiral Dopants for Ferroelectric Mixtures", Buchecker et al. Liquid Crystals, vol. 8, No. 2, pp. 217-227, 1990.

"Induced Smectic C* Phase Concentration Dependence of the Ferroelectric Properties and the Effect of a Local Field", Stegemeyer et al. Liquid Crystals, vol. 3, pp. 295-310, 1991.

Primary Examiner—Robert L. Stoll
Assistant Examiner—Shean C. Wu
Attorney, Agent, or Firm—George M. Gould; George W. Johnston

[57] ABSTRACT

Optically active compounds of the formula

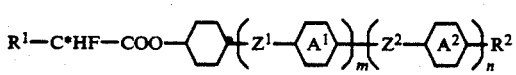

wherein m stands for the number 1 and $R^2$ is an unsubstituted or halogen-substituted alkyl or alkenyl group in which optionally one methylene group is replaced by oxygen and/or optionally one methylene group is replaced by an ester group —COO— or —OOC—; or m stands for the number 0 or 1 and $R^2$ denotes a group of the formula

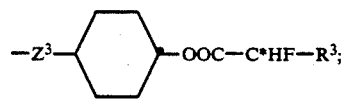

$R^1$ and $R^3$ each independently represent an alkyl or alkenyl group in which optionally one methylene group is replaced by oxygen; $Z^1$, $Z^2$ and $Z^3$ each independently are a single covalent bond, —CH$_2$O—, —OCH$_2$—, —CH$_2$CH$_2$—, —COO— or —OOC—; n stands for the number 0 or 1; rings $A^1$ an $A^2$ each independently are unsubstituted or halogen, cyano and/or methyl-substituted 1,4-phenylene in which optionally 1 CH group or 2 CH groups is/are replaced by nitrogen;

(Abstract continued on next page.)

and C* denotes a chiral carbon atom; with the proviso that simultaneously $R^1$ does not are an alkyl group, m and n do not are the number 1, $Z^1$ does not are the group $-CH_2CH_2-$ or $-CH_2O-$ and ring $A^1$, $Z^2$, ring $A^2$ and $R^2$ together do not are 4-(5-alkyl-2-pyrimidinyl)-phenyl, their preparation, liquid crystalline mixtures which contain these compounds and their use for electro-optical purposes.

8 Claims, No Drawings

LIQUID CRYSTALLINE MIXTURES HAVING A CHIRAL TILTED SMECTIC PHASE

This application is a continuation of application Ser. No. 07/346,189, filed May 2, 1989 now abandoned.

FIELD OF THE INVENTION

The present invention is concerned with novel compounds, their manufacture, liquid crystalline mixtures, especially mixtures having a chiral tilted smectic phase, which contain such compounds and with their use for electro-optical purposes.

BACKGROUND OF THE INVENTION

Liquid crystals are suitable as dielectrics in indicating devices, since their optical properties can be influenced by an electric potential. Suitable electro-optical devices are well-known to the person skilled in the art. Examples of such devices are cells having dynamic scattering, DAP cells (deformation of aligned phases), TN cells (twisted-nematic) and STN cells (super twisted-nematic) having a twisted nematic structure, guest/host cells, phase change cells having a cholesteric-nematic phase transition and SBE cells (super birefringence effect).

Further, electro-optical devices based on chiral tilted smectic liquid crystals are Proposed in Appl. Phys. Lett. 36. 899 (1980) and in Recent Developments in Condensed Matter Physics 4, 309 (1981). In this case the ferroelectric properties of these materials are made use of. As the tilted smectic phases there are suitable, for example, smectic C, F, G, H, I and K Phases. There are generally preferred smectic C phases which, in particular, permit high response speeds. The chiral tilted phases are usually denoted by $S^*_C$, $S^*_F$ etc., with the asterisk indicating the chirality.

Ferroelectric liquid crystals should have a good stability towards chemical and thermal influences and towards electrical fields. Further, they should have a suitable mesophase over a broad temperature range, low viscosity and especially a sufficiently high spontaneous polarization.

Suitable mixtures of ferroelectric liquid crystals include one or more optically active doping substances and a liquid crystal material which may include one or more components and which as a rule should have a tilted smectic phase. The optically active doping substances need not themselves be smectic, but in the liquid crystal material they should produce a chiral tilted smectic phase and should induce a high spontaneous polarization. In order to achieve a high spontaneous polarization in the mixture and/or in order to hold the amount of optically active doping substances relatively low, doping substances which already, in small amounts, are capable of inducing a high spontaneous polarization are desired.

On the other hand, the pitch of the liquid crystal should be distinctly greater than the plate separation of the cell which is used and should typically amount to at least about 10 μm in order to obtain bistable displays which switch well. Optically active doping substances for ferroelectric liquid crystals should therefore preferably induce in the mixture a chiral tilted smectic phase having not only a high spontaneous polarization but a comparatively small twisting (that is, with a large pitch).

SUMMARY OF THE INVENTION

The invention is concerned with optically active compounds of formula

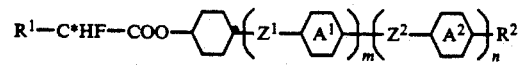

I wherein m stands for the number 1 and $R^2$ is an unsubstituted or halogen-substituted alkyl or alkenyl group in which optionally at least one methylene group is replaced by oxygen or optionally one methylene group is replaced by an ester group —COO— or —OOC—; or m stands for the number 0 or 1 and $R^2$ is a group of the formula

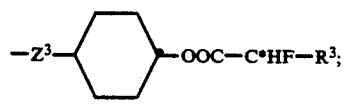

II $R^1$ and $R^3$ each independently are an alkyl or alkenyl group in which optionally one methylene group is replaced by oxygen; $Z^1$, $Z^2$ and $Z^3$ each independently are a single covalent bond, —CH$_2$O—, —OCH$_2$—, —CH—COO— or —OOC—; n stands for the number 0 or 1; rings $A^1$ and $A^2$ each independently are 1,4-phenylene which is unsubstituted or substituted with at least one of halogen cyano or methyl, the 1,4-phenylene optionally having 1 CH group or 2 CH groups replaced by nitrogen; and C* denotes a chiral carbon atom; provided that simultaneously $R^1$ is not an alkyl group, m and n are not the number 1, $Z^1$ is not the group —CH$_2$CH$_2$— or —CH$_2$O— and ring $A^1$, $Z^2$, ring $A^2$ and $R^2$ together are not 4-(5-alkyl-2-pyrimidinyl)-phenyl.

The invention is also concerned with liquid crystalline mixtures which contain the novel compounds of formula I, preparation of the compounds and the use of such compounds for electro-optical purposes.

DETAILED DESCRIPTION OF PREFERRED EMBODIMENTS

The invention is concerned with optically active compounds of the formula

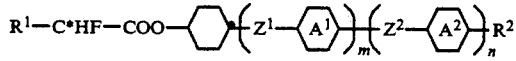

I wherein in m stands for the number 1 and R is an unsubstituted or halogen-substituted alkyl or alkenyl group in which optionally at least one methylene group is replaced by oxygen or optionally one methylene group is replaced by an ester group —COO— or —OOC—; or m stands for the number 0 or 1 and $R^2$ is a group of the formula

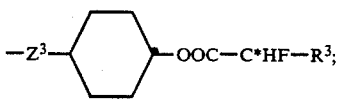

II $R^1$ and $R^3$ each independently are an alkyl or alkenyl group in which optionally one methylene group is replaced by oxygen; $Z^1$, $Z^2$ and $Z^3$ each independently are a single covalent bond, —CH$_2$O—, —OCH$_2$—, —CH$_2$CH$_2$—, —COO— or —OOC—; n stands for the number 0 or 1; rings A$^1$ and A$^2$ each independently are 1,4-phenylene which is unsubstituted or substituted with at least one of halogen cyano or methyl, the 1,4-phenylene optionally having 1 CH group or 2 CH groups replaced by nitrogen; and C* denotes a chiral carbon atom; provided that simultaneously R$^1$ is not an alkyl group, m and n are not the number 1, Z$^1$ is not the group —CH$_2$CH$_2$— or —CH$_2$O— and ring A$^1$, Z$^2$, ring A$^2$ and R$^2$ together are not 4-(5-alkyl-2-pyrimidinyl)-phenyl.

The compounds in accordance with the invention are colourless, have a good solubility in usual liquid crystal materials and as a rule themselves have liquid crystalline properties. Although the chiral α-fluorocarboxylic acid residue is attached to a saturated group, the compounds of formula I induce an amazingly high spontaneous polarization in tilted smectic phases. However, on the other hand surprisingly only a comparatively small twisting is induced in mixtures. In contrast to α-fluorocarboxylic acid phenyl esters, the present α-fluorocarboxylic acid cyclohexyl esters have, moreover, a very good stability.

The term "unsubstituted or halogen-, cyano- and/or methyl-substituted 1,4-phenylene in which optionally 1 CH group or 2 CH groups is/are replaced by oxygen" embraces in the scope of the present invention groups such as 1,4-phenylene, fluoro-1,4-phenylene, chloro-1,4-phenylene, bromo-1,4-phenylene, cyano-1,4-phenylene, 2,3-dicyano-1,4-phenylene, 2,3-difluoro-1,4-phenylene, methyl-1,4-phenylene, pyridine-2,5-diyl, pyrimidine-2,5-diyl, pyrazine-2,5-diyl, pyridazine-3,6-diyl and the like.

The term "halogen" embraces fluorine, chlorine, bromine and iodine, especially fluorine, chlorine and bromine.

The term "unsubstituted or halogen-substituted alkyl or alkenyl group in which optionally one methylene group is replaced by oxygen and/or optionally one methylene group is replaced by an ester group —COO— or —OOC—" embraces unsubstituted or halogen (especially fluorine or chlorine)-substituted alkyl, alkenyl, alkoxy, alkenyloxy, alkoxyalkyl, alkoxycarbonyl, alkenyloxycarbonyl, alkanoyloxy, alkenoyloxy, alkoxyalkoxycarbonyl, alkoxyalkanoyloxy groups and the like, especially alkyl, alkenyl, alkoxy, alkenyloxy, alkoxycarbonyl, alkenyloxycarbonyl, alkanoyloxy, alkenoyloxy, 2-fluoroalkyl, 2-chloroalkyl, 2-fluoroalkoxy, 2-chloroalkoxy, 2-fluoroalkoxycarbonyl, 2-chloroalkoxycarbonyl, 2-fluroalkanoyloxy and 2-chloroalkanoyloxy. An optionally present oxygen atom and an optionally present ester group can additionally form a carbonate group; they are, however, preferably not immediately adjacent. The groups can be straight-chain or branched (for example, n-alkyl, n-alkoxy, isoalkyl, isoalkoxy) and can have the location of the radical in the 1-position (insofar as not expressly indicated the location of the radical hereinafter is in each case in the 1-position) or in the chain, for example, in the 2-position (such as 2-alkyl, 2-alkoxy, 2-alkoxycarbonyl). The groups preferably have a maximum of 15 carbon atoms, for example 2-15 carbon atoms. Examples of preferred groups are methyl, ethyl, propyl, butyl, pentyl hexyl, heptyl, octyl, nonyl, decyl, isopropyl, isobutyl, 2-butyl, 2-octyl, 2-methylbutyl, 3-methylpentyl, vinyl, 1-propenyl, 1-butenyl, 1-pentenyl, allyl, 2-butenyl, 2-pentenyl, 3-butenyl, 3-pentenyl, 4-pentenyl, 5-hexenyl, 6-heptenyl, methoxy, ethoxy, propyloxy, butyloxy, pentyloxy, hexyloxy, heptyloxy, octyloxy, nonyloxy, decyloxy, isopropyloxy, isobutyloxy, 2-butyloxy, 2-octyloxy, 2-methylbutyloxy, 3-methylpentyloxy, allyloxy, 2E-butenyloxy, 3-butenyloxy, 4-pentenyloxy, 5-hexenyloxy, 6-heptenyloxy, 2-fluoro-1-propyloxy, 2-chloro-1-propyloxy, 2-fluoro-1-butyloxy, 2-chloro-1-butyloxy, 2-fluoro- propanoyloxy, 2-chloro-propanoyloxy, 2-fluorobutanoyloxy, 2-chlorobutanoyloxy, 2-fluoropentanoyloxy, 2-chloropentanoyloxy, 2-fluorohexanoyloxy, 2-chlorohexanoyloxy, 2-fluoroheptanoyloxy, 2-chloroheptanoyloxy, 2-fluorooctanoyloxy, 2-chlorooctanoyloxy, 2-octyloxycarbonyl and the like.

The term "alkyl or alkenyl group in which optionally one methylene group is replaced by oxygen" embraces alkyl, alkenyl, alkoxy, alkenyloxy, alkoxyalkyl, alkenyloxyalkyl and alkoxyalkenyl, especially alkyl, alkenyl, alkoxyalkyl and alkenyloxyalkyl. The groups can be straight-chain or branched and can have the location of the radical in the 1-position or in the chain. The groups preferably have about 1-15 carbon atoms, especially about 3-15 carbon atoms. Examples of preferred groups are the examples given above for alkyl, alkenyl etc. In general, straight-chain residues are preferred, especially the straight-chain residues which have the location of the radical in the 1-position or 2-position.

When n in formula I above is the number, 1, m conveniently stands for the number 1 (m=0, n=1 embraces the same compounds as m=1, n=0).

If R$^2$ is a group of formula II, then the two α-fluorocarboxylic acid residues preferably have the same configuration at the α-C atom.

Formula I above therefore embraces optically active compounds of the formula

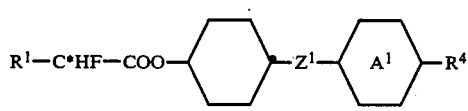

Ia

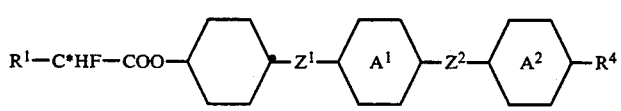

Ib

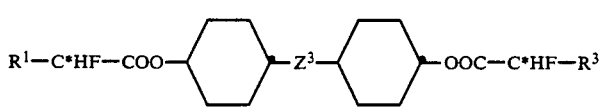

Ic

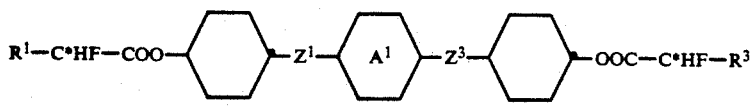

Id

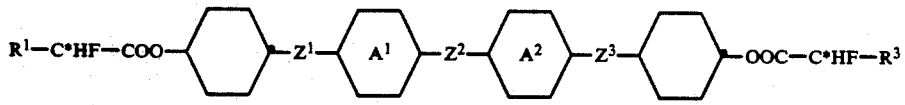

Ie wherein $R^1$, $R^3$, $Z^1$, $Z^2$, $Z^3$, C* rings $A^1$ and $A^2$ are as described above; $R^4$ denotes an unsubstituted or halogen-substituted alkyl or alkenyl group in which optionally one methylene group is replaced by oxygen and/or optionally one methylene group is replaced by an ester group —COO— or —OOC—; with the proviso that in formula Ib simultaneously $R^1$ does not are an alkyl group, $Z^1$ does not are the group —CH or —CH$_2$O— and ring $A^1$, $Z^2$, ring $A^2$ and $R^4$ together do not are 4-(5-alkyl-2-pyrimidinyl)phenyl.

Preferably, rings $A^1$ and $A^2$ in formulas I, Ia, Ib, Id and Ie each independently are 1,4-phenylene, fluoro-1,4-phenylene, chloro-1,4-phenylene, bromo-1,4phenylene, cyano-1,4-phenylene, 2,3-difluoro-1,4phenylene, pyridine-2,5-diyl or pyrimidine-2,5-diyl. Of the compounds of formulas I, Ib and Ie there are generally especially preferred those in which one or both of rings and $A^2$ is 1,4-phenylene, pyrimidine-2,5-diyl, fluoro-1,4-phenylene, chloro-1,4-phenylene, 2,3-difluoro-1,4-phenylene and/or cyano-1,4-phenylene, especially 1,4-phenylene. As a rule there are especially preferred those compounds of formulas I and Ia-Ie in which one of rings $A^1$ and $A^2$ is 1 4-phenylene, fluoro-1,4-phenylene or 2,3-difluoro-1,4-phenylene and the other of rings $A^1$ and $A^2$ is 1,4-phenylene or pyrimidine-2,5-diyl.

Examples of preferred groups of compounds in accordance with the invention are the optically active compounds of the formulas

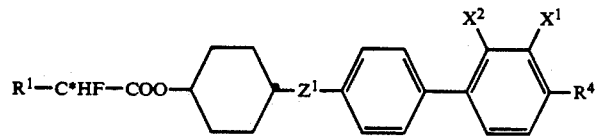

I-1

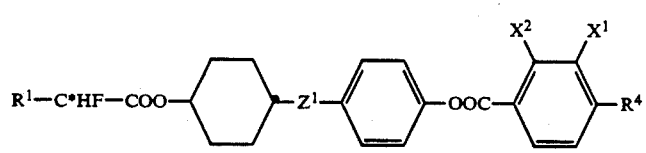

I-2

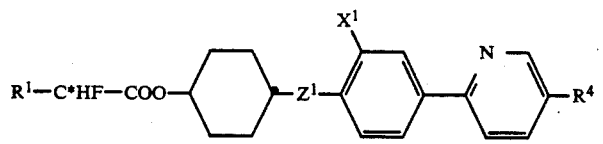

I-3

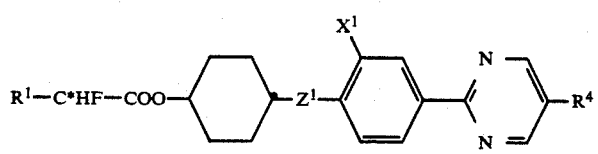

I-4

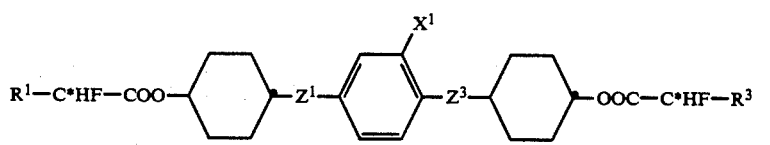

I-5

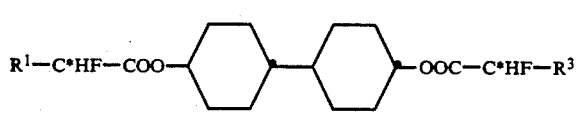

I-6

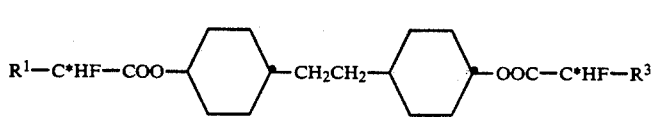

I-7 wherein $R^1$, $R^3$, $R^4$, $Z^1$, $Z^3$ and C* are as described above; $X^1$ and $X^2$ are hydrogen, fluorine, chlorine, bromine, cyano or methyl; with the proviso that in formula I-4 $X^1$ denotes fluorine, chlorine, bromine, cyano or methyl when $Z^1$ represents —CH$_2$CH$_2$— or —CH$_2$O—, $Z^1$ in each of formulas I, Ia, Ib, Id, Ie and I-1 to I-5 above preferably is a single covalent bond, —CH$_2$O—, —CH or —COO—. $Z^3$ in each of formulas II, Id, Ie and I-5 above preferably is a single covalent bond, —OCH$_2$—, —CH or —OOC—. Z in formulas I, Ib and Ie above preferably is a single covalent bond, —COO— or —OOC—. Further, in formulas I-1 and I-2 at least one of the substituents $X^1$ and $X^2$ preferably stands for hydrogen or fluorine; as a rule there are especially preferred those compounds in which $X^1$ is hydrogen, fluorine chlorine, bromine or cyano and $X^2$ is hydrogen as well as those compounds in which $X^1$ is hydrogen or fluorine and $X^2$ is fluorine.

Preferred residues $R^1$ in formulas I, Ia to Ie and I-1 to I-7 are alkyl, alkenyl, alkoxyalkyl and alkenyloxyalkyl, especially alkyl. The residues $R^1$ can be straight-chain or branched and generally have a maximum of 15 carbon atoms, preferably 3-15 carbon atoms and particularly 3-8 carbon atoms. Examples of preferred residues $R^1$ are propyl, isopropyl, butyl, 2-butyl, pentyl, 2-pentyl, allyl, 3-butenyl, 4-pentenyl, alkoxymethyl such as methoxymethyl or ethoxymethyl, alkenyloxymethyl such as allyloxymethyl or (3-butenyl)oxymethyl, 1-alkoxyethyl such as 1-methoxyethyl or 1-ethoxyethyl, 1-alkenyloxyethyl such as 1-allyloxyethyl or 1-(3-butenyl)oxyethyl, 2-alkoxyethyl such as 2-methoxyethyl or 2-ethoxyethyl, 2-alkenyloxyethyl such as 2-allyloxyethyl or 2-(3-butenyl)oxyethyl and the like.

Preferred residues $R^3$ in formulas II, Ic, Id, Ie and I-4 to I-7 above are alkyl, alkenyl, alkoxyalkyl and alkenyloxyalkyl, especially alkyl. The residues $R^3$ can be straight-chain or branched and generally have a maximum of 15 carbon atoms, preferably 3-15 carbon atoms and particularly 3-8 carbon atoms. Examples of preferred residues for $R^3$ are the residues given above for $R^1$ $R^1$ and $R^3$ can be different or preferably also have the same significance.

If desired, chiral residues $R^1$ and, respectively, $R^3$ can preferably also be present in optically active form. Preferably, that configuration which increases the spontaneous polarization of the compound is chosen.

Especially preferred residues $R^1$ and $R^3$ are 1-alkyl and 2-alkyl (=1-methylalkyl). 2-Alkyl residues preferably have the S-configuration when the adjacent group —C*HF— has the S-form and the R-configuration when the adjacent group —C*HF— has the R-form.

$R^2$ in formula I above is a residue $R^4$ or a group of formula II. In formula II $R^3$ and $Z^3$ preferably have one of the preferred significances given above.

Preferred residues $R^4$ in the above formulas Ia, Ib, I-1, I-2, I-3 and I-4 (and, respectively, preferred residues $R^2$ in formula I) are alkyl, alkenyl, alkoxy, alkenyloxy, haloalkoxy (preferably 2-fluoroalkoxy or 2-chloroalkoxy), alkoxycarbonyl and haloalkanoyloxy (preferably 2-fluoroalkanoyloxy or 2-chloroalkanoyloxy), especially alkyl, alkenyl, alkoxy, alkenyloxy and 2-chloroalkoxy. The residues $R^4$ can be straight-chain or branched and preferably have a maximum of 15, for example 2-15, carbon atoms and particularly about 3-10 carbon atoms. Examples of Preferred residues $R^4$ are the groups referred to earlier. Especially preferred residues $R^4$ are alkenyl, alkenyloxy and particularly alkyl and alkoxy.

The compounds of formula I can be prepared in accordance with the invention by esterifying an optically active α-fluorocarboxylic acid of the formula

$$R^1\text{—C*HF—COOH} \qquad \text{III}$$

and a cyclohexanol derivative of the formula

IV wherein m stands for the number 1 and $R^5$ denotes an unsubstituted or halogen-substituted alkyl or alkenyl group in which optionally one methylene group is replaced by oxygen and/or optionally one methylene group is replaced by an ester group —COO— or —OOC—; or m stands for the number 0 or 1 and $R^5$ denotes a group of the formula

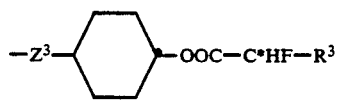

II or

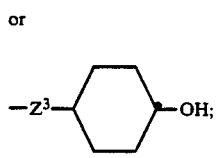

V $R^1$ and $R^3$ each independently represent an alkyl or alkenyl group in which optionally one methylene group is replaced by oxygen; $Z^1$, $Z^2$ and $Z^3$ each independently are a single covalent bond. —CH$_2$O—, —OCH$_2$—, —CH$_2$CH$_2$—, —COO— or —OOC—; n stands for the number 0 or 1; rings $A^1$ and $A^2$ each independently are unsubstituted or halogen-, cyano- and/or methyl-substituted 1,4-phenylene in which optionally 1 CH group or 2 CH groups is/are replaced by nitrogen; and C* denotes a chiral carbon atom; with the proviso that simultaneously R does not are an alkyl group, m and n do not are the number 1, $Z^1$ does not are the group —CH$_2$CH$_2$— or —CH$_2$O— and ring $A^1$, $Z^2$, ring $A^2$ and $R^5$ together do not are 4-(5-alkyl-2-pyrimidinyl)-phenyl, or suitable derivatives of these compounds.

The esterification of the compounds of formulas III and IV or suitable derivatives of these compounds can be effected in a manner known per se according to methods which are described in standard works (for example, Houben-Weyl, Methoden der Organischen Chemie, Georg Thieme Verlag, Stuttgart).

The starting materials of formula IV are known or are analogues of known compounds and can be prepared according to methods which are known to the person skilled in the art. In particular, such cyclohexanol derivatives have already been used for the manufacture of other liquid crystal components.

The optically active α-fluorocarboxylic acids of formula III are also known or are analogues of known compounds and can be prepared according to known methods. For example, they can be obtained from the racemic α-fluorocarboxylic acids by conventional racemate resolution, for example, with ephedrine. Further, racemic and optically active α-fluorocarboxylic acids can be prepared, for example, from α-hydroxycarboxylic acid esters by reaction with diethylaminosulfur trifluoride and subsequent hydrolysis of the ester group. Such methods and starting materials are likewise known from standard works such as Houben-Weyl, Methoden der Organischen Chemie, Georg Thieme Verlag, Stuttgart).

Moreover, α-fluorocarboxylic acids are especially readily accessible by reacting amino acids such as norleucine, isoleucine, valine, serine, threonine and the like with sodium nitrite and pyridine hydrofluoride according to the method described in Helv. Chim. Acta 64, 2528 (1981). (Where inversion at the α-C atom is desired, there can for example, firstly be prepared in an analogous manner the α-hydroxy acid, this can then be converted into the mesylate using methyl chloride and the mesylate can be converted into the α-fluorocarboxylic acid using potassium fluoride.) In the case of α-amino acids which do not have a further functional group, such as leucine, isoleucine and valine, this leads directly to the desired α-fluorocarboxylic acids. In the case of hydroxy-α-amino acids, such as serine and threonine, there are obtained in this manner hydroxy-α-fluorocarboxylic acids and, by subsequent esterification of the carboxy group (for example, with diazomethane), hydroxy-α-fluorocarboxylic acid esters. These can be converted into alkoxy- or alkenyloxy-substituted α-fluorocarboxylic acids, for example by etherification with an alkyl bromide or alkenyl bromide and subsequent hydrolysis of the ester group. Further, the hydroxy-α-fluorocarboxylic acid esters can for example, be converted by oxidation with pyridinium chlorochromate into formyl-substituted α-fluoro-carboxylic acid esters and these can be converted into homologous formyl-substituted α-fluorocarboxylic acid esters by reaction with methoxymethyl-triphenylphosphonium chloride and subsequent hydrolysis of the enol ether (this chain-lengthening reaction can be repeated once or several times if desired). The formyl-substituted α-fluoro-carboxylic acid esters can be converted into alkoxy- or alkenyloxy-substituted α-fluorocarboxylic acids for example, by reduction with sodium borohydride, etherification of the hydroxy group with an alkyl bromide or alkenyl bromide and hydrolysis of the ester group. Alternatively, the formyl-substituted α-fluorocarboxylic acids can be converted into α-fluorocarboxylic acid esters of formula III in which $R^1$ is alkyl or alkenyl by a Wittig reaction with an alkyl-triphenylphosphonium bromide, optional catalytic hydrogenation of the double bond and by subsequent hydrolysis of the ester group.

The compounds of formula I can be used as chiral doping substances in liquid crystalline mixtures. The invention is therefore also concerned with a liquid crystalline mixture having at least 2 components, wherein at least one component is an optically active compound of formula I. Conveniently, the mixture contains a liquid crystal material having a nematic, cholesteric or smectic phase and one or more optically active compounds of formula I.

Mixtures having a chiral tilted smectic phase, especially those having a $S^*_C$ phase, are preferred. These mixtures preferably contain a liquid crystal material having a tilted smectic phase (especially a smectic C phase) and one or more optically active compounds of formula I.

The amount of compounds of formula I in the mixtures in accordance with the invention can vary in a wide range and can be, for example, about 0.5–40 wt. %. In general, the preferred concentration depends mainly on the desired values of the spontaneous polarization and the pitch. In general, a range of about 3–20 wt. % is preferred and a range of about 5–15 wt. % is especially preferred.

As further components there come into consideration usual liquid crystal materials. The mixtures in accordance with the invention preferably contain, in addition to one or more compounds of formula I, one or more of the compounds of the following formulas

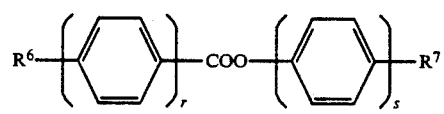

VI

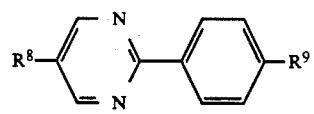

VII

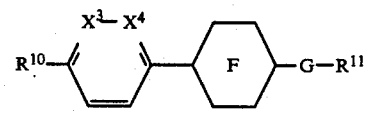

VIII

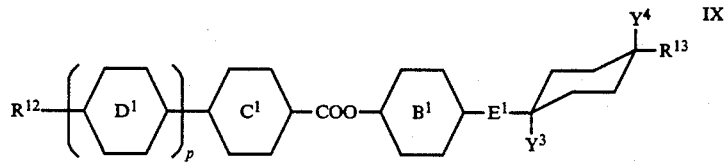

IX

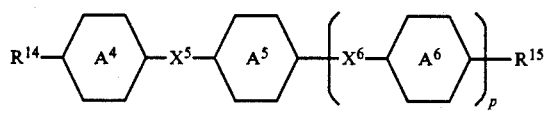

X

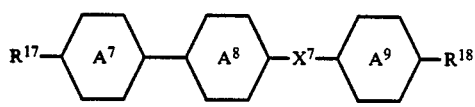

XI

XII wherein $R^6$ and $R^7$ are alkyl, alkoxy, alkanoyl, alkanoyloxy, alkoxycarbonyl or alkoxycarbonyloxy with up to 18 carbon atoms; r and s each independently are 1 or 2; $R^8$ and $R^9$ represent alkyl or alkoxy with 1-18 carbon atoms; $X^3$ stands for CH and $X^4$ stands for N or $X^3$ stands for N and $X^4$ stands for CH; G is a single covalent bond, trans-1,4-cyclohexylene, cis-4-cyano-trans-1,4-cyclohexylene or 1,4-phenylene which is optionally substituted with halogen or methyl; ring F represents trans-1,4-cyclohexylene, 1,4-phenylene which is optionally substituted with halogen or methyl or, when G is a single covalent bond, also cis-4-cyano-trans-1,4- cyclohexylene; $R^{10}$ and $R^{11}$ each denote an optionally halogen-substituted alkyl or alkenyl group in which optionally one $CH_2$ group or two non-adjacent $CH_2$ groups is/are replaced by —O—, —COO— and/or —OOC—; p stands for the number 0 or 1; $E^1$ is a single covalent bond, —$CH_2$—$CH_2$—, —$OCH_2$—, —COO— or —OOC—; rings $B^1$, $C^1$ and $D^1$ denote 1,4-phenylene which is optionally substituted with cyano, halogen or lower alkyl; $Y^3$ and $Y^4$ are hydrogen or one of the substituents $Y^3$ and $Y^4$ also is cyano; $R^{12}$ and $R^{13}$ each independently represent optionally halogen-substituted $C_1$-$C_{18}$-alkyl or optionally halogen-substituted $C_2$-$C_{18}$-alkenyl in which optionally one $CH_2$ group or two non-adjacent $CH_2$ groups is/are replaced by oxygen; $X^5$ represents a single covalent bond, —COO— or —OOC— and $X^6$ represents a single covalent bond, —COO—, —OOC—, —$CH_2CH_2$—, —$OCH_2$— or —$CH_2O$—; rings $A^4$, $A^5$ and $A^6$ each independently are unsubstituted or cyano-, halogen- or lower alkyl-substituted 1 4-phenylene or one of the rings also is pyrimidine- 2 5-diyl or pyrazine-2,5-diyl and/or, when p stands for the number 1, one of the rings also is trans-1,4-cyclohexylene or trans-m-dioxane-2,5-diyl; $R^{14}$ is an optionally halogen-substituted alkenyl group with up to 18 carbon atoms in which optionally 1 $CH_2$ group or 2 non-adjacent $CH_2$ groups is/are replaced by —O—, —CO—, —COO— or —OOC— and/or optionally one C—C single bond is replaced by a C—C double bond; $R^{15}$ is an optionally halogen-substituted alkyl group with up to 18 carbon atoms in which optionally 1 $CH_2$ group or 2 non-adjacent CH groups is/are replaced by —O—, —CO—, —COO— or —OOC— and/or optionally one C—C single bond is replaced by a C—C double bond; $X^7$ denotes a single covalent bond, —COO—, —OOC—, —$CH_2CH_2$—, —$OCH_2$— or —$CH_2O$—; one of rings $A^7$, $A^8$ and $A^9$ represents pyrimidine-2,5-diyl, one of rings $A^7$, $A^8$ and $A^9$ represents unsubstituted or cyano-, halogen- or lower alkyl-substituted 1,4-phenylene and one of rings $A^7$, $A^8$ and $A^9$ represents trans-1,4-cyclohexylene or unsubstituted or cyano-, halogen- or lower alkyl-substituted 1,4-phenylene; and $R^{17}$ and $R^{18}$ each independently are an optionally halogen-substituted alkyl group with up to 18 carbon atoms in which optionally 1 $CH_2$ group or 2 non-adjacent $CH_2$ groups is/are replaced by —O—, —CO—, —COO— and/or —OOC—; $X^8$ denotes a single covalent bond, —COO—, —OOC—, —$CH_2CH_2$—, —$OCH_2$— or —$CH_2O$—; one of dioxane-2,5-diyl and the other two of rings $A^{10}$, $A^{11}$ and $A^{12}$ each independently represent unsubstituted or cyano-, halogen- or lower alkyl-substituted 1,4-phenylene; $R^{19}$ and $R^{20}$ each independently are an optionally halogen-substituted alkyl group with up to 18 carbon atoms in which optionally 1 $CH_2$ group or 2 non-adjacent $CH_2$ groups is/are replaced by —O—, —CO—, —COO— and/or —OOC—.

The manufacture of the liquid crystalline mixtures and of the electro-optical devices can be effected in a manner known per se.

The invention is illustrated in more detail by the following Examples. Optical antipodes have in each case the same phase transition temperatures and induce absolutely the same spontaneous polarization values and twisting values, but with opposite signs. The abbreviations used for the characterization of the phase transitions have the following significances:

C stands for crystalline
S stands for smectic
$S_A$,$S_B$ etc. stand for smectic A, B etc.
$S^*_C$,$S^*_F$ stand for chiral smectic C, F etc.
Ch stands for cholesteric
N stands for nematic
I stands for isotropic.

The following Examples illustrate the present invention but are nor intended to limit its extent in any manner. While the examples describe what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

Unless otherwise stated, percentages and ratios relating to solvent mixtures are expressed in volume, purity data determined by gas chromatography are expressed in area %, and the remaining percentages and ratios are expressed in weight. Temperatures are in degrees Celsius (° C). normal pressure is about 1 atmosphere, and room temperature is about 23° C. Examples were carried out as written unless indicated otherwise.

EXAMPLE 1

0.16 g of (S)-2-fluorohexanoic acid (S-α-fluorocaproic acid), 0.52 g of trans-4-(4'-decyl-4-biphenylyl)cyclohexanol and 0.02 g of 4-(dimethylamino)pyridine were dissolved in 50 ml of dichloromethane and the solution was treated portionwise within 10 minutes while stirring with 0.35 g of N,N'-dicyclohexylcarbodiimide. The mixture was stirred at room temperature overnight and then filtered. The filtrate was diluted with dichloromethane, washed twice with 50 ml of saturated sodium carbonate solution each time and then with water, dried over magnesium sulfate, filtered and subsequently concentrated. The crude product obtained was purified by chromatography on silica gel with hexane/ethyl acetate (vol. 9:1). The trans-4-(4'-decyl-4-biphenylyl)cyclohexyl (S)-2-fluoro-hexanoate was recrystallized from methanol; m.p. (C-S) −80° C., transition S-S −26° C., cl.p. (S-I) 144.5° C., The trans-4-(4'-decyl-4-biphenylyl)cyclohexanol used as the starting material was prepared as follows:

(a) A suspension of 10 g of 4-(4'-cyano-4-biphenylyl)-cyclohexanone, 30 ml of diethyl ether and 270 ml of methanol was treated portionwise at 0° C. with 1.8 g of sodium borohydride. After 3 hours the reaction mixture was made acid (pH 1-2) with 25% hydrochloric acid. The reaction mixture was extracted three times with 50 ml of dichloromethane each time. The combined organic phases were washed twice with 500 ml of water each time and subsequently dried over magnesium sulfate, filtered and concentrated. Recrystallization from methanol gave 3.5 g of trans-4-(4'-cyano-4-biphenylyl)cyclohexanol.

(b) A solution of 3.0 g of trans-4-(4'-cyano-4-biphenylyl)cyclohexanol, 1.1 ml of 3,4-dihydro-2H-pyran in 30 ml of dichloromethane was treated at 0° C. with a solution of 0.007 g of bistrimethylsilyl sulfate in 2 ml of dichloromethane. The reaction mixture was stirred at 0° C. for a further 30 minutes and then washed once with sodium carbonate solution and twice with water and subsequently dried over magnesium sulfate, filtered and concentrated. The crude product was purified by chromatography on silica gel with toluene/ethyl acetate (vol. 9:1). Recrystallization from ethyl acetate at −20° C. gave 1.75 g of pure trans-4-(4'-cyano-4-biphenylyl)cyclohexyl tetrahydropyranyl ether.

(c) A solution of nonylmagnesium bromide (8.3 mmol) in 30 ml of diethyl ether was treated at 0° C. with a solution of 1.5 g of trans-4-(4'-cyano-4-biphenylyl)cyclohexyl tetrahydropyranyl ether in 15 ml of tetrahydrofuran. The reaction mixture was heated at slight reflux overnight and then treated with dilute sodium carbonate solution. The organic phase was separated and the aqueous phase was back-extracted three times with 50 ml of diethyl ether each time. The combined organic phases were washed once with dilute sodium carbonate solution and twice with water and then dried over magnesium sulfate, filtered and concentrated. The residue was purified by chromatography on silica gel with toluene/ethyl acetate (vol. 9:1). The trans-4-(4-decanoyl-4-biphenylyl)cyclohexyl tetrahydropyranyl ether (1.8 g) obtained was used in the next step without further purification.

(d) A mixture of 1.8 g of trans-4-(4-decanoyl-4-biphenylyl)cyclohexyl tetrahydropyranyl ether, 0.2 g of palladium/carbon (5%), 20 ml of toluene and 2 ml of ethanol was stirred for 16 hours while conducting hydrogen through the mixture. Subsequently, the inorganic material was filtered off and the filtrate was concentrated. The residue was purified by chromatography on silica gel with toluene/ethyl acetate (vol. 9:1). The trans-4-(4'-decyl-4-biphenylyl)cyclohexyl tetrahydropyranyl ether (1.2 g) obtained was used in the next step without further purification.

(e) A solution of 1.2 g of trans-4-(4'-decyl-4-biphenylyl)cyclohexyl tetrahydropyranyl ether in 40 ml of methanol and 2 ml of diethyl ether was treated with a solution of 7.3 mg of bistrimethylsilyl sulfate in 2 ml of dichloromethane. The reaction mixture was stirred at room temperature for 2 hours and then treated with 0.2 ml of pyridine. Subseguently, the reaction mixture was concentrated and the residue was then taken up in 50 ml of dichloromethane, washed twice with water, dried over magnesium sulfate, filtered and again concentrated. The residue was purified by chromatography on silica gel with toluene/ethyl acetate (vol. 9:1). Recrystallization from methanol gave 0.5 g of trans-4-(4'-decyl-4-biphenylyl)cyclohexanol.

The following compounds can be prepared in an analogous manner:

trans-4-(4'-Methyl-4-biphenylyl)cyclohexyl (S)-2-fluorohexanoate;
trans-4-(4'-ethyl-4-biphenylyl)cyclohexyl (S)-2-fluorohexanoate;
trans-4-(4'-propyl-4-biphenylyl)cyclohexyl (S)-2-fluorohexanoate;
trans-4-(4'-butyl-4-biphenylyl)cyclohexyl (S)-2-fluorohexanoate;
trans-4-(4'-pentyl-4-biphenylyl)cyclohexyl (S)-2-fluorohexanoate:
trans-4-(4'-hexyl-4-biphenylyl)cyclohexyl (S)-2-fluorohexanoate;
trans-4-(4'-heptyl-4-biphenylyl)cyclohexyl (S)-2-fluorohexanoate;
trans-4-(4'-octyl-4-biphenylyl)cyclohexyl (S)-2-fluorohexanoate;
trans-4-(4'-nonyl-4-biphenylyl)cyclohexyl (S)-2-fluorohexanoate;
trans-4-(4'-methoxy-4-biphenylyl)cyclohexyl (S)-2-fluorohexanoate;
trans-4-(4'-ethoxy-4-biphenylyl)cyclohexyl (S)-2-fluorohexanoate;
trans-4-(4'-propyloxy-4-biphenylyl)cyclohexyl (S)-2-fluorohexanoate;
trans-4-(4'-butyloxy-4-biphenylyl)cyclohexyl (S)-2-fluorohexanoate;
trans-4-(4'-pentyloxy-4-biphenylyl)cyclohexyl (S)-2-fluorohexanoate:
trans-4-(4'-hexyloxy-4-biphenylyl)cyclohexyl (S)-2-fluorohexanoate;
trans-4-(4'-octyloxy-4-biphenylyl)cyclohexyl (S)-2-fluorohexanoate;
trans-4-(4'-nonyloxy-4-biphenylyl)cyclohexyl (S)-2-fluorohexanoate;
trans-4-(4'-decyloxy-4-biphenylyl)cyclohexyl (S)-2-fluorohexanoate;
trans-4-(3'-fluoro-4'-methoxy-4-biphenylyl)cyclohexyl (S)-2-fluorohexanoate;
trans-4-(3'-fluoro-4'-ethoxy-4-biphenylyl)cyclohexyl (S)-2-fluorohexanoate;
trans-4-(3'-fluoro-4'-propyloxy 4-biphenylyl)cyclohexyl (S)-2-fluorohexanoate;
trans-4-(3'-fluoro-4'-butyloxy-4-biphenylyl)cyclohexyl (S)-2-fluorohexanoate;
trans-4-(3'-fluoro-4'-pentyloxy-4-biphenylyl)cyclohexyl (S)-2-fluorohexanoate;
trans-4-(3'-fluoro-4'-hexyloxy-4-biphenylyl)cyclohexyl (S)-2-fluorohexanoate;
trans-4-(3'-fluoro-4'-heptyloxy-4-biphenylyl)cyclohexyl (S)-2-fluorohexanoate;

trans-4-(3'-fluoro-4'-octyloxy-4-biphenylyl)cyclohexyl (S)-2 fluorohexanoate;
trans-4-(3'-fluoro-4'-nonyloxy-4-biphenylyl)cyclohexyl (S)-2-fluorohexanoate;
trans-4-(3'-fluoro-4'-decyloxy-4-biphenylyl)cyclohexyl (S)-2-fluorohexanoate;
trans-4-(2',3'-difluoro-4'-methoxy-4-biphenylyl)cyclohexyl (S)-2-fluorohexanoate;
trans-4-(2',3'-difluoro-4'-ethoxy-4-biphenylyl)cyclohexyl (S)-2-fluorohexanoate;
trans-4-(2',3'-difluoro-4'-propyloxy-4-biphenylyl)cyclohexyl (S)-2-fluorohexanoate;
trans-4-(2',3'-difluoro-4'-butyloxy-4-biphenylyl)cyclohexyl (S)-2-fluorohexanoate;
trans-4-(2',3'-difluoro-4'-pentyloxy-4-biphenylyl)cyclohexyl (S)-2-fluorohexanoate;
trans-4-(2',3'-difluoro-4'-hexyloxy-4-biphenylyl)cyclohexyl (S)-2-fluorohexanoate;
trans-4-(2',3'-difluoro-4'-heptyloxy-4-biphenylyl)cyclohexyl (S)-2-fluorohexanoate;
trans-4-(2',3'-difluoro-4'-octyloxy-4-biphenylyl)cyclohexyl (S)-2-fluorohexanoate;
trans-4-(2',3'-difluoro-4'-nonyloxy-4-biphenylyl)cyclohexyl (S)-2-fluorohexanoate;
trans-4-(2',3'-difluoro-4'-decyloxy-4-biphenylyl)cyclohexyl (S)-2-fluorohexanoate;
trans-4-(3'-chloro-4'-methoxy-4-biphenylyl)cyclohexyl (S)-2-fluorohexanoate;
trans-4-(3'-chloro-4'-ethoxy-4-biphenylyl)cyclohexyl (S)-2-fluorohexanoate;
trans-4-(3'-chloro-4'-propyloxy-4-biphenylyl)cyclohexyl (S)-2-fluorohexanoate;
trans-4-(3'-chloro-4'-butyloxy-4-biphenylyl)cyclohexyl (S)-2-fluorohexanoate;
trans-4-(3'-chloro-4'-pentyloxy-4-biphenylyl)cyclohexyl (S)-2-fluorohexanoate;
trans-4-(3'-chloro-4'-hexyloxy-4-biphenylyl)cyclohexyl (S)-2-fluorohexanoate;
trans-4-(3'-chloro-4'-heptyloxy-4-biphenylyl)cyclohexyl (S)-2-fluorohexanoate;
trans-4-(3'-chloro-4'-octyloxy-4-biphenylyl)cyclohexyl (S)-2-fluorohexanoate;
trans-4-(3'-chloro-4'-nonyloxy-4-biphenylyl)cyclohexyl (S)-2-fluorohexanoate;
trans-4-(3'-chloro-4'-decyloxy-4-biphenylyl)cyclohexyl (S)-2-fluorohexanoate;
trans-4-(3'-bromo-4'-methoxy-4-biphenylyl)cyclohexyl (S)-2-fluorohexanoate;
trans-4-(3'-bromo-4'-ethoxy-4-biphenylyl)cyclohexyl (S)-2-fluorohexanoate:
trans-4-(3'-bromo-4'-propyloxy-4-biphenylyl)cyclohexyl (S)-2-fluorohexanoate;
trans-4-(3'-bromo-4'-butyloxy-4-biphenylyl)cyclohexyl (S)-2-fluorohexanoate;
trans-4-(3'-bromo-4'-pentyloxy-4-biphenylyl)cyclohexyl (S)-2-fluorohexanoate;
trans-4-(3'-bromo-4'-hexyloxy-4-biphenylyl)cyclohexyl (S)-2-fluorohexanoate;
trans-4-(3'-bromo-4'-heptyloxy-4-biphenylyl)cyclohexyl (S)-2-fluorohexanoate;
trans-4-(3'-bromo-4'-octyloxy-4-biphenylyl)cyclohexyl (S)-2-fluorohexanoate;
trans-4-(3'-bromo-4'-nonyloxy-4-biphenylyl)cyclohexyl (S)-2-fluorohexanoate;
trans-4-(3'-bromo-4'-decyloxy-4-biphenylyl)cyclohexyl (S)-2-fluorohexanoate;
trans-4-(3'-cyano-4'-methoxy-4-biphenylyl)cyclohexyl (S)-2-fluorohexanoate;
trans-4-(3'-cyano-4'-ethoxy-4-biphenylyl)cyclohexyl (S)-2-fluorohexanoate;
trans-4-(3'-cyano-4'-propyloxy-4-biphenylyl)cyclohexyl (S)-2-fluorohexanoate;
trans-4-(3'-cyano-4'-butyloxy-4-biphenylyl)cyclohexyl (S)-2-fluorohexanoate;
trans-4-(3'-cyano-4'-pentyloxy-4-biphenylyl)cyclohexyl (S)-2-fluorohexanoate;
trans-4-(3'-cyano-4'-hexyloxy-4-biphenylyl)cyclohexyl (S)-2-fluorohexanoate;
trans-4-(3'-cyano-4'-heptyloxy-4-biphenylyl)cyclohexyl (S)-2-fluorohexanoate;
trans-4-(3'-cyano-4'-octyloxy-4-biphenylyl)cyclohexyl (S)-2-fluorohexanoate;
trans-4-(3'-cyano-4'-nonyloxy-4-biphenylyl)cyclohexyl (S)-2-fluorohexanoate;
trans-4-(3'-cyano-4'-decyloxy-4-biphenylyl)cyclohexyl (S)-2-fluorohexanoate;
trans-4-(2-[4'-methyl-4-biphenylyl]ethyl)cyclohexyl (S)-2-fluorohexanoate;
trans-4-(2-[4'-ethyl-4-biphenylyl]ethyl)cyclohexyl (S)-2-fluorohexanoate;
trans-4-(2-[4'-propyl-4-biphenylyl]ethyl)cyclohexyl (S)-2-fluorohexanoate;
trans-4-(2-[4'-butyl-4-biphenylyl]ethyl)cyclohexyl (S)-2-fluorohexanoate;
trans-4-(2-[4'-pentyl-4-biphenylyl]ethyl)cyclohexyl (S)-2-fluorohexanoate:
trans-4-(2-[4'-hexyl-4-biphenylyl]ethyl)cyclohexyl (S)-2-fluorohexanoate;
trans-4-(2-[4'-heptyl-4-biphenylyl]ethyl)cyclohexyl (S)-2-fluorohexanoate;
trans-4-(2-[4'-octyl-4-biphenylyl]ethyl)cyclohexyl (S)-2-fluorohexanoate;
trans-4-(2-[4'-nonyl-4-biphenylyl]ethyl)cyclohexyl (S)-2-fluorohexanoate;
trans-4-(2-[4'-decyl-4-biphenylyl]ethyl)cyclohexyl (S)-2-fluorohexanoate,
trans-4-(2-[4'-methoxy-4-biphenylyl]ethyl)cyclohexyl (S)-2-fluorohexanoate;
trans-4-(2-[4'-ethoxy-4-biphenylyl]ethyl)cyclohexyl (S)-2-fluorohexanoate;
trans-4-(2-[4'-propyloxy-4-biphenylyl]ethyl)cyclohexyl (S)-2-fluorohexanoate;
trans-4-(2-[4'-butyloxy-4-biphenylyl]ethyl)cyclohexyl (S)-2-fluorohexanoate;
trans-4-(2-[4'-pentyloxy-4-biphenylyl]ethyl)cyclohexyl (S)-2-fluorohexanoate;
trans-4-(2-[4'-hexyloxy-4-biphenylyl]ethyl)cyclohexyl (S)-2-fluorohexanoate;
trans-4-(2-[4'-heptyloxy-4-biphenylyl]ethyl)cyclohexyl (S)-2-fluorohexanoate;
trans-4-(2-[4'-octyloxy-4-biphenylyl]ethyl)cyclohexyl (S)-2-fluorohexanoate;
trans-4-(2-[4'-nonyloxy-4-biphenylyl]ethyl)cyclohexyl (S)-2-fluorohexanoate:
trans-4-(2-[4'-decyloxy-4-biphenylyl]ethyl)cyclohexyl (S)-2-fluorohexanoate;
trans-4-(2-[4'-undecyloxy-4-biphenylyl]ethyl)cyclohexyl (S))-2-fluorohexanoate;
trans-4-(2-[4'-dodecyloxy-4-biphenylyl]ethyl)cyclohexyl (S)-2-fluorohexanoate;
trans-4-(2-[3'-fluoro-4'-methoxy-4-biphenylyl]ethyl)cyclohexyl (S)-2-fluorohexanoate;
trans-4-(2-[3'-fluoro-4'-ethoxy-4-biphenylyl]ethyl)cyclohexyl (S)-2-fluorohexanoate;

trans-4-(2-[3'-fluoro-4'-propyloxy-4-biphenylyl]ethyl)-cyclohexyl (S)-2-fluorohexanoate;
trans-4-(2-[3'-fluoro-4'-butyloxy-4-biphenylyl]ethyl)cyclohexyl (S)-2-fluorohexanoate;
trans-4-(2-[3'-fluoro-4'-pentyloxy-4-biphenylyl]ethyl)-cyclohexyl (S)-2-fluorohexanoate;
trans-4-(2-[3'-fluoro-4'-hexyloxy-4-biphenylyl]ethyl)cyclohexyl (S)-2-fluorohexanoate;
trans-4-(2-[3'-fluoro-4'-heptyloxy-4-biphenylyl]ethyl)-cyclohexyl (S)-2-fluorohexanoate;
trans-4-(2-[3'-fluoro-4'-octyloxy-4-biphenylyl]ethyl)cyclohexyl (S)-2-fluorohexanoate;
trans-4-(2-[3'-fluoro-4'-nonyloxy-4-biphenylyl]ethyl)cyclohexyl (S)-2-fluorohexanoate;
trans-4-(2-[3'-fluoro-4'-decyloxy-4-biphenylyl]ethyl)cyclohexyl (S)-2-fluorohexanoate;
trans-4-(2-[3'-fluoro-4'undecyloxy-4-biphenylyl]ethyl)-cyclohexyl (S)-2-fluorohexanoate;
trans-4-(2-[3'-fluoro-4'-dodecyloxy-4-biphenylyl]ethyl)-cyclohexyl (S)-2-fluorohexanoate;
trans-4-(2-[3'-chloro-4'-methoxy-4-biphenylyl]ethyl)cyclohexyl (S)-2-fluorohexanoate;
trans-4-(2-[3'-chloro-4'-ethoxy-4-biphenylyl]ethyl)cyclohexyl (S)-2-fluorohexanoate;
trans-4-(2-[3'-chloro-4'-propyloxy-4-biphenylyl]ethyl)-cyclohexyl (S)-2-fluorohexanoate;
trans-4-(2-[3'-chloro-4'-butyloxy-4-biphenylyl]ethyl)cyclohexyl (S)-2-fluorohexanoate;
trans-4-(2-[3'-chloro-4'-pentyloxy-4-biphenylyl]ethyl)-cyclohexyl (S)-2-fluorohexanoate;
trans-4-(2-[3'-chloro-4'-hexyloxy-4-biphenylyl]ethyl)cyclohexyl (S)-2-fluorohexanoate;
trans-4-(2-[3'-chloro-4'-heptyloxy-4-biphenylyl]ethyl)-cyclohexyl (S)-2-fluorohexanoate;
trans-4-(2-[3'-chloro-4'-4-octyloxy-4-biphenylyl]ethyl)-cyclohexyl (S)-2-fluorohexanoate: trans-4-(2-[3'-chloro-4'-nonyloxy-4-biphenylyl]ethyl)cyclohexyl (S)-2-fluorohexanoate;
trans-4-(2-[3'-chloro-4'-decyloxy-4-biphenylyl]ethyl)-cyclohexyl (S)-2-fluorohexanoate;
trans-4-(2-[3'-bromo-4'-methoxy-4-biphenylyl]ethyl)cyclohexyl (S)-2-fluorohexanoate;
trans-4-(2-[3'-bromo-4'-ethoxy-4-biphenylyl]ethyl)cyclohexyl (S)-2-fluorohexanoate;
trans-4-(2-[3'-bromo-4'-propyloxy-4-biphenylyl]ethyl)-cyclohexyl (S)-2-fluorohexanoate;
trans-4-(2-[3'-bromo-4'-butyloxy-4-biphenylyl]ethyl)cyclohexyl (S)-2-fluorohexanoate;
trans-4-(2-[3'-bromo-4'-pentyloxy-4-biphenylyl]ethyl)-cyclohexyl (S)-2-fluorohexanoate;
trans-4-(2-[3'-bromo-4'-hexyloxy-4-biphenylyl]ethyl)cyclohexyl (S)-2-fluorohexanoate;
trans-4-(2-[3'-bromo-4'-heptyloxy-4-biphenylyl]ethyl)-cyclohexyl (S)-2-fluorohexanoate;
trans-4-(2-[3'-bromo-4'-octyloxy-4-biphenylyl]ethyl)cyclohexyl (S)-2-fluorohexanoate;
trans-4-(2-[3'-bromo-4'-nonyloxy-4-biphenylyl]ethyl)-cyclohexyl (S)-2-fluorohexanoate;
trans-4-(2-[3'-bromo-4'-decyloxy-4-biphenylyl]ethyl)-cyclohexyl (S)-2-fluorohexanoate;
trans-4-(2-[3'-cyano-4-methoxy-4-biphenylyl]ethyl)cyclohexyl (S)-2-fluorohexanoate;
trans-4-(2-[3'-cyano-4'-ethoxy-4-biphenylyl]ethyl)cyclohexyl (S)-2-fluorohexanoate;
trans-4-(2-[3'-cyano-4'-propyloxy-4-biphenylyl]ethyl)-cyclohexyl (S)-2-fluorohexanoate;
trans-4-(2-[3'-cyano-4'-butyloxy-4-biphenylyl]ethyl)cyclohexyl (S)-2-fluorohexanoate:
trans-4-(2-[3'-cyano-4'-pentyloxy-4-biphenylyl]ethyl)-cyclohexyl (S)-2-fluorohexanoate;
trans-4-(2-[3'-cyano-4'-hexyloxy-4-biphenylyl]ethyl)cyclohexyl (S)-2-fluorohexanoate;
trans-4-(2-[3'-cyano-4'-heptyloxy-4-biphenylyl]ethyl)-cyclohexyl (S)-2-fluorohexanoate;
trans-4-(2-[3'-cyano-4'-octyloxy-4-biphenylyl]ethyl)cyclohexyl (S)-2-fluorohexanoate;
trans-4-(2-[3'-cyano-4'-nonyloxy-4-biphenylyl]ethyl)cyclohexyl (S)-2-fluorohexanoate;
trans-4-(2-[3'-cyano-4'-decyloxy-4-biphenylyl]ethyl)cyclohexyl (S)-2-fluorohexanoate;
trans-4-[2-(4'-[(S)-2-octyloxy]-4-biphenylyl)ethyl]cyclohexyl (S)-2-fluorohexanoate:
trans-4-[2-(3'-fluoro-4'-[(S)-2-octyloxy]-4-biphenylyl)ethyl]cyclohexyl (S)-2-fluorohexanoate;
trans-4-[2-(3'-chloro-4'-[(S)-2-octyloxy]-4-biphenylyl)ethyl]cyclohexyl (S)-2-fluorohexanoate;
trans-4-[2-(3'-bromo-4'-[(S)-2-octyloxy]-4-biphenylyl)ethyl]cyclohexyl (S)-2-fluorohexanoate;
trans-4-[2-(3'-cyano-4'[(S)-2-octyloxy]-4-biphenylyl)ethyl]cyclohexyl (S)-2-fluorohexanoate;
trans-4-[2-(4'-[(R)-2-octyloxy]-4-biphenylyl)ethyl]cyclohexyl (S)-2-fluorohexanoate;
trans-4-[2-(3'-fluoro-4'-[(R)-2-octyloxy]-4-biphenylyl)ethyl]cyclohexyl (S)-2-fluorohexanoate;
trans-4-[2-(3'-chloro-4'-[(R)-2-octyloxy]-4-biphenylyl)ethyl]cyclohexyl (S)-2-fluorohexanoate;
trans-4-[2-(3'-bromo-4'-[(R)-2-octyloxy]-4-biphenylyl)ethyl]cyclohexyl (S)-2-fluorohexanoate;
trans-4-[2-(3'-cyano-4'-[(R)-2-octyloxy]-4-biphenylyl)ethyl]cyclohexyl (S)-2-fluorohexanoate;
trans-4-[2-(4'-[(S)-2-chloro-1-propyloxy]-4-biphenylyl)ethyl]cyclohexyl (S)-2-fluorohexanoate;
trans-4-[2-(4'-[(S)-2-chloro-1-propyloxy]-4-biphenylyl)ethyl]cyclohexyl (R)-2-fluorohexanoate:
trans-4-[2-(4'-[(R)-2-chloro-1-propyloxy]-4-biphenylyl)ethyl]cyclohexyl (S)-2-fluorohexanoate;
trans-4-[2-(4'-[(R)-2-chloro-1-propyloxy]-4-biphenylyl)ethyl]cyclohexyl (R)-2-fluorohexanoate;
trans-4-(4-methoxyphenyl)cyclohexyl (S)-2-fluorohexanoate;
trans-4-(4-ethoxyphenyl)cyclohexyl (S)-2-fluorohexanoate;
trans-4-(4-propyloxyphenyl)cyclohexyl (S)-2-fluorohexanoate;
trans-4-(4-butyloxyphenyl)cyclohexyl (S)-2-fluorohexanoate;
trans-4-(4-pentyloxyphenyl)cyclohexyl (S)-2-fluorohexanoate;
trans-4-(4-hexyloxyphenyl)cyclohexyl (S)-2-fluorohexanoate;
trans-4-(4-heptyloxyphenyl)cyclohexyl (S)-2-fluorohexanoate;
trans-4-(4-octyloxyphenyl)cyclohexyl (S)-2-fluorohexanoate;
trans-4-(4-nonyloxyphenyl)cyclohexyl (S)-2-fluorohexanoate;
trans-4-(4-decyloxyphenyl)cyclohexyl (S)-2-fluorohexanoate, m.p. (C-I) 42.5° C., cl.p. ($S_B$-I) 41° C.;
trans-4-(4-undecyloxyphenyl)cyclohexyl (S)-2-fluorohexanoate;
trans-4-(4-dodecyloxyphenyl)cyclohexyl (S)-2-fluorohexanoate.

The compounds listed hereinafter are prepared in an analogous manner by esterifying trans-4-[4-(5-alkyl-2-pyrimidinyl)phenyl]cyclohexanols; the starting materials were obtained by reducing 4-(4-cyanophenyl)cyclohexanone with sodium borohydride and reacting the resulting trans-4-(4-cyanophenyl)cyclohexanol in an analogous manner to Z. Naturforschung 34b, 1535 (1979):

trans-4-[4-(5-Methyl-2-pyrimidinyl)phenyl]cyclohexyl (S)-2-fluorohexanoate;
trans-4-[4-(5-ethyl-2-pyrimidinyl)phenyl]cyclohexyl (S)-2-fluorohexanoate;
trans-4-[4-(5-propyl-2-pyrimidinyl)phenyl]cyclohexyl (S)-2-fluorohexanoate;
trans-4-[4-(5-butyl-2-pyrimidinyl)phenyl]cyclohexyl (S)-2-fluorohexanoate;
trans-4-[4-(5-pentyl-2-pyrimidinyl)phenyl]cyclohexyl (S)-2-fluorohexanoate;
trans-4-[4-(5-hexyl-2-pyrimidinyl)phenyl]cyclohexyl (S)-2-fluorohexanoate, m.p. (C-$S_B$) 34° C., transition ($S_B$-$S_A$) 98° C. cl.p. ($S_A$-I) 137° C.;
trans-4-[4-(5-heptyl-2-pyrimidinyl)phenyl]cyclohexyl (S)-2-fluorohexanoate, m.p. (C-$S_B$) 53° C., transition ($S_B$-$S_A$) 101° C., cl.p. ($S_A$-I) 143° C;
trans-4-[4-(5-octyl-2-pyrimidinyl)phenyl]cyclohexyl (S)-2-fluorohexanoate, m.p. (C-$S_B$) 41° C. transition ($S_B$-$S_A$) 109° C., cl.p. ($S_A$-I) 143° C.;
trans-4-[4-(5-nonyl-2-pyrimidinyl)phenyl]cyclohexyl (S)-2-fluorohexanoate, m.p. (C-$S_B$) 49° C., transition ($S_B$-$S_A$) 113° C., cl.p. ($S_A$I) 145° C.;
trans-4-[4-(5-decyl-2-pyrimidinyl)phenyl]cyclohexyl (S)-2-fluorohexanoate, m.p. (C-$S_B$) 48° C., transition ($S_B$-$S_A$) 116° C., cl.p. ($S_A$-I) 145° C.;
trans-4-[4-(5-methyl-2-pyrimidinyl)phenyl]cyclohexyl (2S,3S)-2-fluoro-3-methylpentanoate;
trans-4-[4-(5-ethyl-2-pyrimidinyl)phenyl]cyclohexyl (2S,3S)-2-fluoro-3-methylpentanoate:
trans-4-[4-(5-propyl-2-pyrimidinyl)phenyl]cyclohexyl (2S,3S)-2-fluoro-3-methylpentanoate;
trans-4-[4-(5-butyl-2-pyrimidinyl)phenyl]cyclohexyl (2S,3S)-2-fluoro-3-methylpentanoate;
trans-4-[4-(5-pentyl-2-pyrimidinyl)phenyl]cyclohexyl (2S,3S)-2-fluoro-3-methylpentanoate:
trans-4-[4-(5-hexyl-2-pyrimidinyl)phenyl]cyclohexyl (2S,3S)-2-fluoro-3-methylpentanoate;
trans-4-[4-(5-heptyl-2-pyrimidinyl)phenyl]cyclohexyl (2S,3S)-2-fluoro-3-methylpentanoate;
trans-4-[4-(5-octyl-2-pyrimidinyl)phenyl]cyclohexyl (2S,3S)-2-fluoro-3-methylpentanoate;
trans-4-[4-(5-nonyl-2-pyrimidinyl)phenyl]cyclohexyl (2S,3S)-2-fluoro-3-methylpentanoate;
trans-4-[4-(5-decyl-2-pyrimidinyl)phenyl]cyclohexyl (2S,3S)-2-fluoro-3-methylpentanoate.

The compounds listed hereinafter can be prepared in an analogous manner by esterifying trans-4-(4'-alkoxy-2',3'-difluoro-4-biphenylyl)cyclohexanols; the starting materials were obtained according to known methods by the etherification of 2,3-difluorophenol with an alkyl bromide, subsequent reaction with butyllithium and the monoketal of bicyclohexyl-4,4'-dione with ethylene glycol, dehydration with toluenesulfonic acid, reaction with 2,3-dichloro-5,6-dicyano-1,4-benzoquinone, hydrolysis of the ketal group and reduction of the resulting ketone with sodium borohydride to the alcohol:

trans-4-(4'-Methoxy-2',3'-difluoro-4-biphenylyl)cyclohexyl (S)-2-fluorohexanoate;
trans-4-(4'-ethoxy-2',3'-difluoro-4-biphenylyl)cyclohexyl (S)-2-fluorohexanoate;
trans-4-(4'-propyloxy-2',3'-difluoro-4-biphenylyl)cyclohexyl (S)-2-fluorohexanoate;
trans-4-(4'-butyloxy-2',3'-difluoro-4-biphenylyl)cyclohexyl (S)-2-fluorohexanoate;
trans-4-(4'-pentyloxy-2',3'-difluoro-4-biphenylyl)cyclohexyl (S)-2-fluorohexanoate;
trans-4-(4'-hexyloxy-2',3'-difluoro-4-biphenylyl)cyclohexyl (S)-2-fluorohexanoate;
trans-4-(4'-heptyloxy-2',3'-difluoro-4-biphenylyl)cyclohexyl (S)-2-fluorohexanoate;
trans-4-(4'-octyloxy-2',3'-difluoro-4-biphenylyl)cyclohexyl (S)-2-fluorohexanoate;
trans-4-(4'-nonyloxy-2',3'-difluoro-4-biphenylyl)cyclohexyl (S)-2-fluorohexanoate;
trans-4-(4'-decyloxy-2',3'-difluoro-4-biphenylyl)cyclohexyl (S)-2-fluorohexanoate;
trans-4-(4'-methoxy-2',3'-difluoro-4-biphenylyl)cyclohexyl (2S,3S)-2-fluoro-3-methylpentanoate:
trans-4-(4'-ethoxy-2',3'-difluoro-4-biphenylyl)cyclohexyl (2S,3S)-2-fluoro-3-methylpentanoate;
trans-4-(4'-propyloxy-2',3'-difluoro-4-biphenylyl)cyclohexyl (2S,3S)-2-fluoro-3-methylpentanoate;
trans-4-(4'-butyloxy-2',3'-difluoro-4-biphenylyl)cyclohexyl (2S,3S)-2-fluoro-3-methylpentanoate;
trans-4-(4'-pentyloxy-2',3'-difluoro-4-biphenylyl)cyclohexyl (2S,3S)-2-fluoro-3-methylpentanoate:
trans-4-(4'-hexyloxy-2',3'-difluoro-4-biphenylyl)cyclohexyl (2S,3S)-2-fluoro-3-methylpentanoate;
trans-4-(4'-heptyloxy-2',3'-difluoro-4-biphenylyl)cyclohexyl (2S,3S)-2-fluoro-3-methylpentanoate:
trans-4-(4'-octyloxy-2',3'-difluoro-4-biphenylyl)cyclohexyl (2S,3S)-2-fluoro-3-methylpentanoate;
trans-4-(4'-nonyloxy-2',3'-difluoro-4-biphenylyl)cyclohexyl (2S,3S)-2-fluoro-3-methylpentanoate;
trans-4-(4'-decyloxy-2',3'-difluoro-4-biphenylyl)cyclohexyl (2S,3S)-2-fluoro-3-methylpentanoate.

EXAMPLE 2

0.2 g of (S)-2-fluorohexanoic acid (S-α-fluorocaproic acid), 0.5 g of trans-4-([2-bromo-4-(5-decyl-2-pyrimidinyl)phenoxy]methyl)cyclohexanol, 0.35 g of N,N'-dicyclohexylcarbodiimide, 0.02 g of 4-(dimethylamino)pyridine and 50 ml of dichloromethane were reacted in an analogous manner to Example 1. This gave 0.4 g of trans-4-([2-bromo-4-(5-decyl-2-pyrimidinyl)phenoxy]methyl)cyclohexyl (S)-2-fluorohexanoate.

The trans-4-([2-bromo-4-(5-decyl-2-pyrimidinyl)phenoxy]methyl)cyclohexanol used as the starting material was prepared as follows:

(a) A solution of 5 g of 4-(5-decyl-2-pyrimidinyl)phenol in 50 ml of dichloromethane was treated at 0° C. while gassing with argon with a solution of 2.6 g of bromine in 50 ml of dichloromethane. The reaction mixture was stirred for a further 2 hours and then treated with water. The organic phase was separated and the aqueous phase was back-extracted three times with 50 ml of dichloromethane each time. The combined organic phases were washed with water, sodium hydrogen carbonate solution and again with water, dried over magnesium sulfate, filtered and subsequently concentrated. The residue was purified by chromatography on silica gel with toluene/ethyl acetate (vol. 4:1). Recrystallization from hexane gave 4.8 g of 2-bromo-4-(5-decyl-2-pyrimidinyl)phenol.

(b) A mixture of 4.8 g of 2-bromo-4-(5-decyl-2-pyrimidinyl)phenol. 3.5 g of (trans-4-hydroxycyclohexyl)methyl tosylate, 6.8 g of potassium carbonate and 100 ml of butanone was heated under slight reflux for 2 days. Subsequently, the cooled reaction mixture was poured into water and extracted three times with 50 ml of dichloromethane each time. The combined organic phases were washed with water, dried over magnesium sulfate, filtered and subsequently concentrated. The residue was purified by chromatography on silica gel with toluene/ethyl acetate (vol. 4:1). This gave 4.5 g of trans-4-([2-bromo-4-(5-decyl-2-pyrimidinyl)-phenoxy]methyl)cyclohexanol.

The following compounds can be prepared in an analogous manner:

trans-4-([2-fluoro-4-(5-methyl-2-pyrimidinyl)phenoxy]methyl)cyclohexyl (S)-2-fluorohexanoate;
trans-4-([2-fluoro-4-(5-ethyl-2pyrimidinyl)phenoxy]methyl)cyclohexyl (S)-2-fluorohexanoate;
trans-4-([2-fluoro-4-(5propyl-2pyrimidinyl)phenoxy]methyl)cyclohexyl ((S)-2-fluorohexanoate;
trans-4-([2-fluoro-4-(5-butyl-2-pyrimidinyl)phenoxy]methyl)cyclohexyl (S)-2-fluorohexanoate;
trans-4-([2-fluoro-4-(5pentyl-2pyrimidinyl)phenoxy]methyl)cyclohexyl (S)-2-fluorohexanoate;
trans-4-([2-fluoro-4-(5-hexyl-2-pyrimidinyl)phenoxy]methyl)cyclohexyl (S)-2-fluorohexanoate;
trans-4-([2-fluoro-4-(5-heptyl-2-pyrimidinyl)phenoxy]methyl)cyclohexyl (S)-2-fluorohexanoate;
trans-4-([2-fluoro-4-(5-octyl-2-pyrimidinyl)phenoxy]methyl)cyclohexyl (S)-2-fluorohexanoate;
trans-4-([2-fluoro-4-(5-nonyl-2-pyrimidinyl)phenoxy]methyl)cyclohexyl (S)-2-fluorohexanoate;
trans-4-([2-fluoro-4-(5-decyl-2-pyrimidinyl)phenoxy]methyl)cyclohexyl (S)-2-fluorohexanoate;
trans-4-([2-chloro-4-(5-methyl-2pyrimidinyl)phenoxy]methyl)cyclohexyl (S)-2-fluorohexanoate;
trans-4-([2-chloro-4-(5-ethyl-2pyrimidinyl)phenoxy]methyl)cyclohexyl (S)-2-fluorohexanoate;
trans-4-([2-chloro-4-(5propyl-2-pyrimidinyl)phenoxy]methyl)cyclohexyl (S)-2-fluorohexanoate;
trans-4-([2-chloro-4-(5-butyl-2-pyrimidinyl)phenoxy]methyl)cyclohexyl (S)-2-fluorohexanoate;
trans-4-([2-chloro-4-(5pentyl-2-pyrimidinyl)phenoxy]methyl)cyclohexyl (S)-2-fluorohexanoate;
trans-4-([2-chloro-4-(5-hexyl-2-pyrimidinyl)phenoxy]methyl)cyclohexyl (S)-2-fluorohexanoate;
trans-4-([2-chloro-4-(5-heptyl-2-pyrimidinyl)phenoxy]methyl)cyclohexyl (S)-2-fluorohexanoate;
trans-4-([2-chloro-4-(5-octyl-2-pyrimidinyl)phenoxy]methyl)cyclohexyl (S)-2-fluorohexanoate;
trans-4-([2-chloro-4-(5-nonyl-2-pyrimidinyl)phenoxy]methyl)cyclohexyl (S)-2-fluorohexanoate;
trans-4-([2-chloro-4-(5-decyl-2-pyrimidinyl)phenoxy]methyl)cyclohexyl (S)-2-fluorohexanoate;
trans-4-([2-bromo-4-(5-methyl-2-pyrimidinyl)phenoxy]methyl)cyclohexyl (S)-2-fluorohexanoate;
trans-4-([2-bromo-4-(5-ethyl-2pyrimidinyl)phenoxy]methyl)cyclohexyl (S)-2-fluorohexanoate;
trans-4-([2-bromo-4-(5propyl-2pyrimidinyl)phenoxy]methyl)cyclohexyl (S)-2-fluorohexanoate;
trans-4-([2-bromo-4-(5-butyl 2pyrimidinyl)phenoxy]methyl)cyclohexyl (S)-2-fluorohexanoate;
trans-4-([2-bromo-4-(5-pentyl-2-pyrimidinyl)phenoxy]methyl)cyclohexyl (S)-2-fluorohexanoate;
trans-4-([2-bromo-4-(5-hexyl-2-pyrimidinyl)phenoxy]methyl)cyclohexyl (S)-2-fluorohexanoate;
trans-4-([2-bromo-4-(5-heptyl-2-pyrimidinyl)phenoxy]methyl)cyclohexyl (S)-2-fluorohexanoate;
trans-4-([2-bromo-4-(5-octyl-2-pyrimidinyl)phenoxy]methyl)cyclohexyl (S)-2-fluorohexanoate;
trans-4-([2-bromo-4-(5-nonyl-2-pyrimidinyl)phenoxy]methyl)cyclohexyl (S)-2-fluorohexanoate;
trans-4-([2-cyano-4-(5-methyl-2pyrimidinyl)phenoxy]methyl)cyclohexyl (S)-2-fluorohexanoate;
trans-4-([2-cyano-4-(5-ethyl-2pyrimidinyl)phenoxy]methyl)cyclohexyl (S)-2-fluorohexanoate;
trans-4-([2-cyano-4-(5propyl-2pyrimidinyl)phenoxy]methyl)cyclohexyl (S)-2-fluorohexanoate;
trans-4-([2-cyano-4-(5-butyl-2pyrimidinyl)phenoxy]methyl)cyclohexyl (S)-2-fluorohexanoate;
trans-4-([2-cyano-4-(5pentyl-2pyrimidinyl)phenoxy]methyl)cyclohexyl (S)-2-fluorohexanoate;
trans-4-([2-cyano-4-(5-hexyl-2-pyrimidinyl)phenoxy]methyl)cyclohexyl (S)-2-fluorohexanoate;
trans-4-([2-cyano-4-(5-heptyl-2pyrimidinyl)phenoxy]methyl)cyclohexyl (S)-2-fluorohexanoate;
trans-4-([2-cyano-4-(5-octyl-2-pyrimidinyl)phenoxy]methyl)cyclohexyl (S)-2-fluorohexanoate;
trans-4-([2-cyano-4-(5-nonyl-2pyrimidinyl)phenoxy]methyl)cyclohexyl (S)-2-fluorohexanoate;
trans-4-([2-cyano-4-(5-decyl-2pyrimidinyl)phenoxy]methyl)cyclohexyl (S)-2-fluorohexanoate;
trans-4-([4'-methyl-4-biphenylyloxy]methyl)cyclohexyl (S)-2-fluorohexanoate;
trans-4-([4'-ethyl-4-biphenylyloxy]methyl)cyclohexyl (S)-2-fluorohexanoate;
trans-4-([4'-propyl-4-biphenylyloxy]methyl)cyclohexyl (S)-2-fluorohexanoate;
trans-4-([4'-butyl-4-biphenylyloxy]methyl)cyclohexyl (S)-2-fluorohexanoate;
trans-4-([4'-pentyl-4-biphenylyloxy]methyl)cyclohexyl (S)-2-fluorohexanoate;
trans-4-([4'-hexyl-4-biphenylyloxy]methyl)cyclohexyl (S)-2-fluorohexanoate;
trans-4-([4'-heptyl-4-biphenylyloxy]methyl)cyclohexyl (S)-2-fluorohexanoate;
trans-4-([4'-octyl-4-biphenylyloxy]methyl)cyclohexyl (S)-2-fluorohexanoate;
trans-4-([4'-nonyl-4-biphenylyloxy]methyl)cyclohexyl (S)-2-fluorohexanoate;
trans-4-([4'-decyl-4-biphenylyloxy]methyl)cyclohexyl (S)-2-fluorohexanoate;
trans-4-([4'-undecyl-4-biphenylyloxy]methyl)cyclohexyl (S)-2-fluorohexanoate;
trans-4-([4'-dodecyl-4-biphenylyloxy]methyl)cyclohexyl (S)-2-fluorohexanoate;
trans-4-([4'-methoxy-4-biphenylyloxy]methyl)cyclohexyl (S)-2-fluorohexanoate,
trans-4-([4'-ethoxy-4-biphenylyloxy]methyl)cyclohexyl (S)-2-fluorohexanoate;
trans-4-([4'-propyloxy-4-biphenylyloxy]methyl)cyclohexyl (S)-2-fluorohexanoate;
trans-4-([4'-butyloxy-4-biphenylyloxy]methyl)cyclohexyl (S)-2-fluorohexanoate;
trans-4-([4'-pentyloxy-4-biphenylyloxy]methyl)cyclohexyl (S)-2-fluorohexanoate;
trans-4-([4'-hexyloxy-4-biphenylyloxy]methyl)cyclohexyl (S)-2-fluorohexanoate;
trans-4-([4'-heptyloxy-4-biphenylyloxy]methyl)cyclohexyl (S)-2-fluorohexanoate;
trans-4-([4'-octyloxy-4-biphenylyloxy]methyl)cyclohexyl (S)-2-fluorohexanoate;
trans-4-([4'-nonyloxy-4-biphenylyloxy]methyl)cyclohexyl (S)-2-fluorohexanoate;
trans-4-([4'-decyloxy-4-biphenylyloxy]methyl)cyclohexyl (S)-2-fluorohexanoate;
trans-4-([3'-fluoro-4'-octyloxy-4-biphenylyloxy]methyl)cyclohexyl (S)-2-fluorohexanoate;
trans-4-([3'-chloro-4'-octyloxy-4-biphenylyloxy]methyl)cyclohexyl (S)-2-fluorohexanoate;

trans-4-([3'-bromo-4'-octyloxy-4-biphenylyloxy]methyl)cyclohexyl (S)-2-fluorohexanoate;
trans-4-(([3'-cyano-4'-octyloxy-4-biphenylyloxy]methyl)cyclohexyl (S)-2-fluorohexanoate;
trans-4-([3'-fluoro-4'-octyloxy-4-biphenylyloxy]methyl)cyclohexyl (R)-2-fluorohexanoate;
trans-4-([3'-chloro-4'-octyloxy-4-biphenylyloxy]methyl)cyclohexyl (R)-2-fluorohexanoate;
trans-4-([3'-bromo-4'-octyloxy-4-biphenylyloxy]methyl)cyclohexyl (R)-2-fluorohexanoate;
trans-4-([3'-cyano-4'-octyloxy-4-biphenylyloxy]methyl)cyclohexyl (R)-2-fluorohexanoate;
trans-4-([4'-[(S)-2-octyloxy]-4-biphenylyloxy]methyl)cyclohexyl (S)-2-fluorohexanoate;
trans-4-([4'-[(S)-2-octyloxy]-4-biphenylyloxy]methyl)cyclohexyl (R)-2-fluorohexanoate;
trans-4-([4-(5-methyl-2-pyridinyl)phenoxy]methyl)cyclohexyl (S)-2-fluorohexanoate;
trans-4-([4-(5-ethyl-2-pyridinyl)phenoxy]methyl)cyclohexyl (S)-2-fluorohexanoate;
trans-4-([4-(5-propyl-2-pyridinyl)phenoxy]methyl)cyclohexyl (S)-2-fluorohexanoate;
trans-4-([4-(5-butyl-2-pyridinyl)phenoxy]methyl)cyclohexyl (S)-2-fluorohexanoate;
trans-4-([4-(5-pentyl-2-pyridinyl)phenoxy]methyl)cyclohexyl (S)-2-fluorohexanoate;
trans-4-([4-(5-hexyl-2-pyridinyl)phenoxy]methyl)cyclohexyl (S)-2-fluorohexanoate;
trans-4-([4-(5-heptyl-2-pyridinyl)phenoxy]methyl)cyclohexyl (S)-2-fluorohexanoate;
trans-4-([4-(5-octyl-2-pyridinyl)phenoxy]methyl)cyclohexyl (S)-2-fluorohexanoate;
trans-4-([4-(5-nonyl-2-pyridinyl)phenoxy]methyl)cyclohexyl (S)-2-fluorohexanoate;
trans-4-([4-(5-decy)-2-pyridinyl)phenoxy]methyl)cyclohexyl (S)-2-fluorohexanoate;
trans-4-([2-fluoro-4-(5-decyl-2-pyridinyl)phenoxy]methyl)cyclohexyl (S)-2-fluorohexanoate;
trans-4-([2-chloro-4-(5-decyl-2-pyridinyl)phenoxy]methyl)cyclohexyl (S)-2-fluorohexanoate;
trans-4-([2-bromo-4-(5-decyl-2-pyridinyl)phenoxy]methyl)cyclohexyl (S)-2-fluorohexanoate;
trans-4-([2-cyano-4-(5-decyl-2-pyridinyl)phenoxy]methyl)cyclohexyl (S)-2-fluorohexanoate.

EXAMPLE 3

0.2 g of (S)-2-fluorohexanoic acid (S-α-fluorocaproic acid), 0.8 g of trans-4-(2-[4-(4-dodecyloxybenzoyloxy)phenyl]ethyl)cyclohexanol, 0.45 g of N,N'-dicyclohexylcarbodiimide, 3 mg of 4-(dimethylamino)pyridine and 30 ml of dichloromethane were reacted in an analogous manner to Example 1. This gave 0.6 g of trans-4-(2-[4-(4-dodecyloxybenzoyloxy)phenyl]ethyl)cyclohexyl (S)-2-fluorohexanoate.

The trans-4-(2-[4-(4-dodecyloxybenzoyloxy)phenyl]ethyl)cyclohexanol used as the starting material was prepared as follows:

(a) A mixture of 5 g of trans-4-hydroxycyclohexanecarboxaldehyde, 30 g of 4-methoxybenzyl-triphenylphosphonium bromide and 250 ml of tert-butyl methyl ether was treated with 7 g of potassium tert-butylate at 0° C. while gassing with argon. The reaction mixture was stirred at room temperature for a further 2 hours and then treated with water. The reaction mixture was extracted three times with 50 ml of diethyl ether each time. The combined organic phases were washed with water, dried over magnesium sulfate, filtered and subsequently concentrated. The residue was treated several times with hexane. The combined organic phases were again concentrated. The crude product obtained was purified by chromatography on silica gel with hexane. This gave 8 g of 1-(trans-4-hydroxycyclohexyl)-2-(4-methoxyphenyl)ethene (cis/trans mixture).

(b) A mixture of 8 g of 1-(trans-4-hydroxycyclohexyl)-2-(4-methoxyphenyl)ethene, 0.5 g of palladium/carbon (5%) and 100 ml of ethyl acetate was reacted in an analogous manner to Example 1 (d) while conducting hydrogen through the mixture. This gave 7.5 g of trans-4-(2-[4-methoxyphenyl]ethyl)cyclohexanol.

(c) A mixture of 7.5 g trans-4-(2-[4-methoxyphenyl]ethyl)cyclohexanol and 100 ml of dichloromethane was treated at 0° C. with 27 ml of a 1M solution of boron tribromide in dichloromethane. The reaction mixture was stirred at room temperature for a further 2 hours and then poured on to ice-water. The organic phase was separated and the aqueous phase was back-extracted three times with 50 ml of dichloromethane each time. The combined organic phases were washed with water, sodium hydrogen carbonate solution and again with water and then dried over magnesium sulfate, filtered and concentrated. The residue was recrystallized from hexane and gave 5.2 g of trans-4-(2-[4-hydroxyphenyl]ethyl)cyclohexanol.

(d) 0.7 g of 4-dodecyloxybenzoic acid, 0.5 g of trans-4-(2-[4-hydroxyphenyl]ethyl)cyclohexanol, 0.6 g of N,N'-dicyclohexylcarbodiimide, 4 mg of 4-(dimethylamino)pyridine and 50 ml of dichloromethane were reacted in an analogous manner to Example 1. This gave 0.8 g of trans-4-(2-[4-(4-dodecyloxybenzoyloxy)phenyl]ethyl)cyclohexanol.

The following compounds can be prepared in an analogous manner:
trans-4-(2-[4-(4-Methoxybenzoyloxy)phenyl]ethyl)cyclohexyl (S)-2-fluorohexanoate;
trans-4-(2-[4-(4-ethoxybenzoyloxy)phenyl]ethyl)cyclohexyl (S)-2-fluorohexanoate;
trans-4-(2-[4-(4-propyloxybenzoyloxy)phenyl]ethyl)cyclohexyl (S)-2-fluorohexanoate;
trans-4-(2-[4-(4-butyloxybenzoyloxy)phenyl]ethyl)cyclohexyl (S)-2-fluorohexanoate;
trans-4-(2-[4-(4pentyloxybenzoyloxy)phenyl]ethyl)cyclohexyl (S)-2-fluorohexanoate;
trans-4-(2-[4-(4-hexyloxybenzoyloxy)phenyl]ethyl)cyclohexyl (S)-2-fluorohexanoate;
trans-4-(2-[4-(4-heptyloxybenzoyloxy)phenyl]ethyl)cyclohexyl (S)-2-fluorohexanoate;
trans-4-(2-[4-(4-octyloxybenzoyloxy)phenyl]ethyl)cyclohexyl (S)-2-fluorohexanoate;
trans-4-(2-[4-(4-nonyloxybenzoyloxy)phenyl]ethyl)cyclohexyl (S)-2-fluorohexanoate;
trans-4-(2-[4-(4-decyloxybenzoyloxy)phenyl]ethyl)cyclohexyl (S)-2-fluorohexanoate;
trans-4-(2-[4-(4-undecyloxybenzoyloxy)phenyl]ethyl)cyclohexyl (S)-2-fluorohexanoate;
trans-4-(2-[4-(4-methylbenzoyloxy)phenyl]ethylcyclohexyl (S)-2-fluorohexanoate;
trans-4-(2-[4-(4-ethylbenzoyloxy)phenyl]ethylcyclohexyl (S)-2-fluorohexanoate;
trans-4-(2-[4-(4propylbenzoyloxy)phenyl]ethylcyclohexyl (S)-2-fluorohexanoate;

trans-4-(2-[4-(4-butylbenzoyloxy)phenyl]ethylcyclohexyl (S)-2-fluorohexanoate;
trans-4-(2-[4-(4pentylbenzoyloxy)phenyl]ethylcyclohexyl (S)-2-fluorohexanoate;
trans-4-(2-[4-(4-hexylbenzoyloxy)phenyl]ethylcyclohexyl (S)-2-fluorohexanoate;
trans-4-(2-[4-(4-heptylbenzoyloxy)phenyl]ethylcyclohexyl (S)-2-fluorohexanoate;
trans-4-(2-[4-(4-octylbenzoyloxy)phenyl]ethylcyclohexyl (S)-2-fluorohexanoate;
trans-4-(2-[4-(4-nonylbenzoyloxy)phenyl]ethylcyclohexyl (S)-2-fluorohexanoate;
trans-4-(2-[4-(4-decylbenzoyloxy)phenyl]ethylcyclohexyl (S)-2-fluorohexanoate;
trans-4-(2-[4-(2-fluoro-4-methoxybenzoyloxy)phenyl]ethyl)cyclohexyl (S)-2-fluorohexanoate;
trans-4-(2-[4-(2-fluoro-4-ethoxybenzoyloxy)phenyl]ethyl)cyclohexyl (S)-2-fluorohexanoate:
trans-4-(2-[4-(2-fluoro-4-propyloxybenzoyloxy)phenyl]ethyl)cyclohexyl (S)-2-fluorohexanoate;
trans-4-(2-[4-(2-fluoro-4-butyloxybenzoyloxy)phenyl]ethyl)cyclohexyl (S)-2-fluorohexanoate;
trans-4-(2-[4-(2-fluoro-4pentyloxybenzoyloxy)phenyl]ethyl)cyclohexyl (S)-2-fluorohexanoate;
trans-4-(2-[4-(2-fluoro-4-hexyloxybenzoyloxy)phenyl]ethyl)cyclohexyl (S)-2-fluorohexanoate;
trans-4-(2-[4-(2-fluoro-4-heptyloxybenzoyloxy)phenyl]ethyl)cyclohexyl (S)-2-fluorohexanoate;
trans-4-(2-[4-(2-fluoro-4-octyloxybenzoyloxy)phenyl]ethyl)cyclohexyl (S)-2-fluorohexanoate;
trans-4-(2-[4-(2-fluoro-4-nonyloxybenzoyloxy)phenyl]ethyl)cyclohexyl (S)-2-fluorohexanoate;
trans-4-(2-[4-(2-fluoro-4-decyloxybenzoyloxy)phenyl]ethyl)cyclohexyl (S)-2-fluorohexanoate;
trans-4-(2-[4-(2-fluoro-4-undecyloxybenzoyloxy)phenyl]ethyl)cyclohexyl (S)-2-fluorohexanoate;
trans-4-(2-[4-(2-fluoro-4-dodecyloxybenzoyloxy)phenyl]ethyl)cyclohexyl (S)-2-fluorohexanoate;
trans-4-(2-[4-(3-fluoro-4-methoxybenzoyloxy)phenyl]ethyl)cyclohexyl (S)-2-fluorohexanoate;
trans-4-(2-[4-(3-fluoro-4-ethoxybenzoyloxy)phenyl]ethyl)cyclohexyl (S)-2-fluorohexanoate;
trans-4-(2-[4-(3-fluoro-4propyloxybenzoyloxy)phenyl]ethyl)cyclohexyl (S)-2-fluorohexanoate;
trans-4-(2-[4-(3-fluoro-4-butyloxybenzoyloxy)phenyl]ethyl)cyclohexyl (S)-2-fluorohexanoate;
trans-4-(2-[4-fluoro-4-pentyloxybenzoyloxy)phenyl]ethyl)cyclohexyl (S)-2-fluorohexanoate;
trans-4-(2-[4-(3-fluoro-4-hexyloxybenzoyloxy)phenyl]ethyl)cyclohexyl (S)-2-fluorohexanoate;
trans-4-(2-[4-(3-fluoro-4-heptyloxybenzoyloxy)phenyl]ethyl)cyclohexyl (S)-2-fluorohexanoate;
trans-4-(2-[4-(3-fluoro-4-octyloxybenzoyloxy)phenyl]ethyl)cyclohexyl (S)-2-fluorohexanoate;
trans-4-(2-[4-(3-fluoro-4-nonyloxybenzoyloxy)phenyl]ethyl)cyclohexyl (S)-2-fluorohexanoate;
trans-4-(2-[4-(3-fluoro-4-decyloxybenzoyloxy)phenyl]ethyl)cyclohexyl (S)-2-fluorohexanoate;
trans-4-(2-[4-(3-fluoro-4-undecyloxybenzoyloxy)phenyl]ethyl)cyclohexyl (S)-2-fluorohexanoate;
trans-4-(2-[4-(3-fluoro-4-dodecyloxybenzoyloxy)phenyl]ethyl)cyclohexyl (S)-2-fluorohexanoate;
trans-4-(2-[4-(2-chloro-4-dodecyloxybenzoyloxy)phenyl]ethyl)cyclohexyl (S)-2-fluorohexanoate;
trans-4-(2-[4-(3-chloro-4-dodecyloxybenzoyloxy)phenyl]ethyl)cyclohexyl (S)-2-fluorohexanoate;
trans-4-(2-[4-(2-bromo-4-dodecyloxybenzoyloxy)phenyl]ethyl)cyclohexyl (S)-2-fluorohexanoate;
trans-4-(2-[4-(3-bromo-4-dodecyloxybenzoyloxy)phenyl]ethyl)cyclohexyl (S)-2-fluorohexanoate;
trans-4-(2-[4-(2-cyano-4-dodecyloxybenzoyloxy)phenyl]ethyl)cyclohexyl (S)-2-fluorohexanoate;
trans-4-(2-[4-(3-cyano-4-dodecyloxybenzoyloxy)phenyl]ethyl)cyclohexyl (S)-2-fluorohexanoate;
trans-4-(2-[4-(2-chloro-4-dodecyloxybenzoyloxy)phenyl]ethyl)cyclohexyl (R)-2-fluorohexanoate;
trans-4-(2-[4-(3-chloro-4-dodecyloxybenzoyloxy)phenyl]ethyl)cyclohexyl (R)-2-fluorohexanoate;
trans-4-(2-[4-(2-bromo-4-dodecyloxybenzoyloxy)phenyl]ethyl)cyclohexyl (R)-2-fluorohexanoate;
trans-4-(2-[4-(3-bromo-4-dodecyloxybenzoyloxy)phenyl]ethyl)cyclohexyl (R)-2-fluorohexanoate;
trans-4-(2-[4-(2-cyano-4-dodecyloxybenzoyloxy)phenyl]ethyl)cyclohexyl (R)-2-fluorohexanoate;
trans-4-(2-[4-(3-cyano-4-dodecyloxybenzoyloxy)phenyl]ethyl)cyclohexyl (R)-2-fluorohexanoate;
trans-4-(2-[4-(4-[(S)-2-chloro-1propyloxy]benzoyloxy)phenyl]ethyl)cyclohexyl (S)-2-fluorohexanoate;
trans-4-(2-[4-(4-[(R)-2-chloro-1-propyloxy]benzoyloxy)phenyl]ethyl)cyclohexyl (S)-2-fluorohexanoate;
trans-4-(2-[4-(4-[(S)-2-chloro-1-propyloxy]benzoyloxy)phenyl]ethyl)cyclohexyl (R)-2-fluorohexanoate;
trans-4-(2-[4-(4-[(R)-2-chloro-1propyloxy]benzoyloxy)phenyl]ethyl)cyclohexyl (R)-2-fluorohexanoate:
trans-4-(4-[4-methoxybenzoyloxy]phenyl)cyclohexyl (S)-2-fluorohexanoate;
trans-4-(4-[4-ethoxybenzoyloxy]phenyl)cyclohexyl (S)-2-fluorohexanoate;
trans-4-(4-[4propyloxybenzoyloxy]phenyl)cyclohexyl (S)-2-fluorohexanoate;
trans-4-(4-[4-butyloxybenzoyloxy]phenyl)cyclohexyl (S)-2-fluorohexanoate;
trans-4-(4-[4pentyloxybenzoyloxy]phenyl)cyclohexyl (S)-2-fluorohexanoate;
trans-4-(4-[4-hexyloxybenzoyloxy]phenyl)cyclohexyl (S)-2-fluorohexanoate;
trans-4-(4-[4-heptyloxybenzoyloxy]phenyl)cyclohexyl (S)-2-fluorohexanoate;
trans-4-(4-[4-octyloxybenzoyloxy]phenyl)cyclohexyl (S)-2-fluorohexanoate;
trans-4-(4-[4-nonyloxybenzoyloxy]phenyl)cyclohexyl (S)-2-fluorohexanoate;
trans-4-(4-[4-decyloxybenzoyloxy]phenyl)cyclohexyl (S)-2-fluorohexanoate;
trans-4-(4-[4-undecyloxybenzoyloxy]phenyl)cyclohexyl (S)-2-fluorohexanoate;
trans-4-(4-[4-dodecyloxybenzoyloxy]phenyl)cyclohexyl (S)-2-fluorohexanoate. m.p. (C-S$_B$) 64° C. transition (S$_B$-S$_A$) 113° C., cl.p. (S$_A$-I) 159° C.;
trans-4-(4-[3-fluoro-4-dodecyloxybenzoyloxy]phenyl)cyclohexyl (S)-2-fluorohexanoate, m.p. (C-S$_C^*$) 73° C., cl.p. (S$_C^*$-I) 148° C.;
trans-4-(4-[3-chloro-4-dodecyloxybenzoyloxy]phenyl)cyclohexyl (S)-2-fluorohexanoate, m.p. (C-S$_C^*$) 50° C., cl.p. (S$_C^*$-I) 138° C.;
trans-4-(4-[3-bromo-4-dodecyloxybenzoyloxy]phenyl)cyclohexyl (S)-2-fluorohexanoate, m.p. (C-S$_C^*$) 56° C., cl.p. (S$_C^*$-I) 118° C.;
trans-4-(4-[3-cyano-4-dodecyloxybenzoyloxy]phenyl)cyclohexyl (S)-2-fluorobenzoic acid;
trans-4-(4-[2,3-difluoro-4-methoxybenzoyloxy]phenyl)cyclohexyl (S)-2-fluorohexanoate;
trans-4-(4-[2,3-difluoro-4-ethoxybenzoyloxy]phenyl)cyclohexyl (S)-2-fluorohexanoate;
trans-4-(4-[2,3-difluoro-4-propyloxybenzoyloxy]phenyl)cyclohexyl (S)-2-fluorohexanoate;

trans-4-(4-[2,3-difluoro-4-butyloxybenzoyloxy]phenyl)-cyclohexyl (S)-2-fluorohexanoate;
trans-4-(4-[2,3-difluoro-4-pentyloxybenzoyloxy]phenyl)cyclohexyl (S)-2-fluorohexanoate;
trans-4-(4-[2,3-difluoro-4-hexyloxybenzoyloxy]phenyl)-cyclohexyl (S)-2-fluorohexanoate;
trans-4-(4-[2,3-difluoro-4-heptyloxybenzoyloxy]phenyl)cyclohexyl (R)-2-fluorohexanoate, m.p. (C-S$_C^*$) 82° C., transition (S$_C^*$-S$_A$) 93° C., transition (S$_A$-Ch) 140° C., cl.p. (Ch-I) 151° C.;
trans-4-(4-[2,3-difluoro-4-octyloxybenzoyloxy]phenyl)-cyclohexyl (S)-2-fluorohexanoate, m.p. (C-S$_C^*$) 77° C. transition (S$_C^*$-S$_A$) 91° C., transition (S$_A$-Ch) 143° C., cl.p. (Ch-I) 150° C.;
trans-4-(4-[2,3-difluoro-4-nonyloxybenzoyloxy]phenyl)-cyclohexyl (R)-2-fluorohexanoate, m.p. (C-S$_C^*$) 74° C., transition (S$_C^*$-S$_A$) 87° C., transition (S$_A$-Ch) 145° C., cl.p. (Ch-I) 148° C.;
trans-4-(4-[2,3-difluoro-4-decyloxybenzoyloxy]phenyl)-cyclohexyl (S)-2-fluorohexanoate, m.p. (C-S$_C^*$) 72° C., transition (S$_C^*$-S$_A$) 84° C., transition (S$_A$-Ch) 147° C., cl.p. (Ch-I) 148° C.;
trans-4-(4-[2,3-difluoro-4-undecyloxybenzoyloxy]cyclohexyl (S)-2-fluorohexanoate, m.p. (C-S$_A$) 78° C., transition (S$_C^*$-S$_A$) 77° C. cl.p. (S$_A$-I) 147° C.;
trans-4-(4-[2,3 difluoro-4-dodecyloxybenzoyloxy]phenyl)cyclohexyl (S)-2-fluorohexanoate, m.p. (C-S$_C^*$) 73° C., transition (S$_C^*$-S$_A$) 74° C., cl.p. (S$_A$-I) 147° C.;
trans-4-(4-[2,3-difluoro-4-methoxybenzoyloxy]phenyl)-cyclohexyl (2S,3S)-2-fluoro-3-methylpentanoate;
trans-4-(4-[2,3-difluoro-4-ethoxybenzoyloxy]phenyl)cyclohexyl (2S,3S)-2-fluoro-3-methylpentanoate;
trans-4-(4-[2,3-difluoro-4-propyloxybenzoyloxy]phenyl)cyclohexyl (2S,3S)-2-fluoro-3-methylpentanoate;
trans-4-(4-[2,3-difluoro-4-butyloxybenzoyloxy]phenyl)-cyclohexyl (2S,3S)-2-fluoro-3-methylpentanoate;
trans-4-(4-[2,3-difluoro-4-pentyloxybenzoyloxy]phenyl)cyclohexyl (2S,3S)-2-fluoro-3-methylpentanoate;
trans-4-(4-[2,3-difluoro-4-hexyloxybenzoyloxy]phenyl)-cyclohexyl (2S,3S)-2-fluoro-3-methylpentanoate;
trans-4-(4-[2,3-difluoro-4-heptyloxybenzoyloxy]phenyl)cyclohexyl (2S,3S)-2-fluoro-3-methylpentanoate;
trans-4-(4-[2,3-difluoro-4-octyloxybenzoyloxy]phenyl)cyclohexyl (2S,3S)-2-fluoro-3-methylpentanoate, m.p. (C-S$_C^*$) 45.2° C., transition (S$_C^*$-S$_A$) 101° C., transition (S$_A$-Ch) 126.2° C., cl.p. (Ch-I) 140.6° C.;
trans-4-(4-[2,3-difluoro-4-nonyloxybenzoyloxy]phenyl)-cyclohexyl (2S,3S)-2-fluoro-3-methylpentanoate;
trans-4-(4-[2,3-difluoro-4-decyloxybenzoyloxy]phenyl)-cyclohexyl (2S,3S)-2-fluoro-3-methylpentanoate;
trans-4-(4-[2,3-difluoro-4-undecyloxybenzoyloxy]phenyl)cyclohexyl (2S,3S)-2-fluoro-3-methylpentanoate;
trans-4-(4-[2,3-difluoro 4-dodecyloxybenzoyloxy]phenyl)cyclohexyl (2S,3S)-2-fluoro-3-methylpentanoate;
trans-4-[(4-[4-methoxybenzoyloxy]phenoxy)methyl]cyclohexyl (S)-2-fluorohexanoate;
trans-4-[(4-[4-ethoxybenzoyloxy]phenoxy)methyl]cyclohexyl (S)-2-fluorohexanoate;
trans-4-[(4-[4propyloxybenzoyloxy]phenoxy)methyl]cyclohexyl (S)-2-fluorohexanoate;
trans-4-[(4-[4-butyloxybenzoyloxy]phenoxy)methyl]cyclohexyl (S)-2-fluorohexanoate;
trans-4-[(4-[4pentyloxybenzoyloxy]phenoxy)methyl]cyclohexyl (S)-2-fluorohexanoate;
trans-4-[(4-[4-hexyloxybenzoyloxy]phenoxy)methyl]cyclohexyl (S)-2-fluorohexanoate;
trans-4-[(4-[4-heptyloxybenzoyloxy]phenoxy)methyl]cyclohexyl (S)-2-fluorohexanoate;
trans-4-[(4-[4-octyloxybenzoyloxy]phenoxy)methyl]cyclohexyl (S)-2-fluorohexanoate;
trans-4-[(4-[4-nonyloxybenzoyloxy]phenoxy)methyl]cyclohexyl (S)-2-fluorohexanoate;
trans-4-[(4-[4-decyloxybenzoyloxy]phenoxy)methyl]cyclohexyl (S)-2-fluorohexanoate;
trans-4-[(4-[4-undecyloxybenzoyloxy]phenoxy)methyl]cyclohexyl (S)-2-fluorohexanoate;
trans-4-[(4-[4-dodecyloxybenzoyloxy]phenoxy)methyl]cyclohexyl (S)-2-fluorohexanoate;
trans-4-[(4-[3-fluoro-4-dodecyloxybenzoyloxy]phenoxy)methyl]cyclohexyl (S)-2-fluorohexanoate;
trans-4-[(4-[3-chloro-4-dodecyloxybenzoyloxy]phenoxy)methyl]cyclohexyl (S)-2-fluorohexanoate;
trans-4-[(4-[3-bromo-4-dodecyloxybenzoyloxy]phenoxy)methyl]cyclohexyl (S)-2-fluorohexanoate;
trans-4-[(4-[3-cyano-4-dodecyloxybenzoyloxy]phenoxy)methyl]cyclohexyl (S)-2-fluorohexanoate;
trans-4-[(4-[2.3-difluoro-4-methoxybenzoyloxy]phenoxy)methyl]cyclohexyl (S)-2-fluorohexanoate;
trans-4-[(4-[2,3-difluoro-4-ethoxybenzoyloxy]phenoxy)methyl]cyclohexyl (S)-2-fluorohexanoate;
trans-4-[(4-[2,3-difluoro-4propyloxybenzoyloxy]phenoxy)methyl]cyclohexyl (S)-2-fluorohexanoate;
trans-4-[(4-[2,3-difluoro-4-butyloxybenzoyloxy]phenoxy)methyl]cyclohexyl (S)-2-fluorohexanoate;
trans-4-[(4-[2,3-difluoro-4pentyloxybenzoyloxy]phenoxy)methyl]cyclohexyl (S)-2-fluorohexanoate;
trans-4-[(4-[2,3-difluoro-4-hexyloxybenzoyloxy]phenoxy)methyl]cyclohexyl (S)-2-fluorohexanoate;
trans-4-[(4-[2,3-difluoro-4-heptyloxybenzoyloxy]phenoxy)methyl]cyclohexyl (S)-2-fluorohexanoate;
trans-4-[(4-[2,3-difluoro 4-octyloxybenzoyloxy]phenoxy)methyl]cyclohexyl (S)-2-fluorohexanoate;
trans-4-[(4-[2,3-difluoro-4-nonyloxybenzoyloxy]phenoxy)methyl] cyclohexyl (S)-2-fluorohexanoate;
trans-4-[(4-[2,3-difluoro-4-decyloxybenzoyloxy]phenoxy)methyl]cyclohexyl (S)-2-fluorohexanoate;
trans-4-[(4-[2,3-difluoro-4-undecyloxybenzoyloxy]phenoxy)methyl]cyclohexyl (S)-2-fluorohexanoate;
trans-4-[(4-[2,3-difluoro-4-dodecyloxybenzoyloxy]phenoxy)methyl]cyclohexyl (S)-2-fluorohexanoate.

EXAMPLE 4

0.23 g of (S)-2-fluorohexanoic acid (S-α-fluorocaproic acid), 0.24 g of trans 4-(4-[(trans-4-hydroxycyclohexyl)methoxy]phenyl)cyclohexanol, 0.29 g of N,N'-dicyclohexylcarbodiimide, 0.02 g of 4-(dimethylamino)pyridine and 20 ml of dichloromethane were reacted in an analogous manner to Example 1. This gave 0.2 g of trans-4-(4-[(trans-4-[(S)-2-fluorohexanoyloxy]cyclohexyl)methoxy]phenyl)cyclohexyl (S)-2-fluorohexanoate; m.p. (C-S) <25° C., transition (S-S$_A$) 67° C., cl.p. (S$_A$-I) 88.9° C.

The trans-4-(4-[(trans-4-hydroxycyclohexyl)methoxy]phenyl)cyclohexanol used as the starting material was prepared as follows:

(a) A mixture of 1.0 g of 4-(4-hydroxyphenyl)cyclohexanone, 1.4 g of (trans-4-hydroxycyclohexyl)methyl tosylate, 1.5 g of potassium carbonate and 60 ml of absolute butanone was heated under reflux for 2 days. Subsequently, the cooled reaction mixture was poured into water and extracted three times with 50 ml of dichloro methane each time. The combined organic phases were washed with water, dried over magnesium sulfate, filtered and subsequently concentrated. The residue was purified by chromatography on silica gel with toluene-/ethyl acetate (Vol. 5:1). This gave 1.0 g of 4-(4-[(trans-4-hydroxycyclohexyl)methoxy] phenyl)cyclohexanone.

(b) 1.0 g of 4-(4-[(trans-4-hydroxycyclohexyl)methoxy]phenyl)cyclohexanone, 0.12 g of sodium borohydride, 20 ml of methanol and 2 ml of diethyl ether were reacted in an analogous manner to Example 1 (a). The crude product was purified by chromatography on silica gel with dichloromethane/methanol (vol. 19:1). This gave 0.24 g of trans-4-(4-[(trans-4-hydroxycyclohexyl)methoxy]-phenyl)cyclohexanol.

The following compounds can be prepared in an analogous manner:

trans-4-(4-[(trans-4-[(S)-2-Fluoropropanoyloxy]cyclohexyl)methoxy]phenyl)cyclohexyl (S)-2-fluoropropanoate;
trans-4-(4-[(trans-4-[(S)-2-fluorobutanoyloxy]cyclohexyl)methoxy]phenyl)cyclohexyl (S)-2-fluorobutanoate;
trans-4-(4-[(trans-4-[(S)-2-fluoropentanoyloxy]cyclohexyl)methoxy]phenyl)cyclohexyl (S)-2-fluoropentanoate;
trans-4-(4-[(trans-4-[(S)-2-fluorohepanoyloxy]cyclohexyl)methoxy]phenyl)cyclohexyl (S)-2-fluoroheptanoate;
trans-4-(4-[(trans-4-[(S)-2-fluorooctanoyloxy]cyclohexyl)methoxy]phenyl)cyclohexyl (S)-2-fluorooctanoate;
trans-4-(4-[(trans-4-[(S)-2-fluorononanoyloxy]cyclohexyl)methoxy]phenyl)cyclohexyl (S)-2-fluorononanoate;
trans-4-(4-[(trans-4-[(S)-2-fluorodecanoyloxy]cyclohexyl)methoxy]phenyl)cyclohexyl (S)-2-fluorodecanoate;
trans-4-(4-[(trans-4-[(R)-2-fluoropropanoyloxy]cyclohexyl)methoxy]phenyl)cyclohexyl (R)-2-fluoropropanoate;
trans-4-(4-[(trans-4-[(R)-2-fluorobutanoyloxy]cyclohexyl)methoxy]phenyl)cyclohexyl (R)-2-fluorobutanoate;
trans-4-(4-[(trans-4-[(R)-2-fluoropentanoyloxy]cyclohexyl)methoxy]phenyl)cyclohexyl (R) 2 fluoropentanoate;
trans-4-(4-[(trans-4-[(R)-2-fluorohexanoyloxy]cyclohexyl)methoxy]phenyl)cyclohexyl (R)-2-fluorohexanoate;
trans-4-(4-[(trans-4-[(R)-2-fluoroheptanoyloxy]cyclohexyl)methoxy]phenyl)cyclohexyl (R)-2-fluoroheptanoate;
trans-4-(4-[(trans-4-[(R)-2-fluorooctanoyloxy]cyclohexyl)methoxy]phenyl)cyclohexyl (R)-2 fluorooctanoate;
trans-4-(4-[(trans-4-[(R)-2-fluorononanoyloxy]cyclohexyl)methoxy]phenyl)cyclohexyl (R)-2-fluorononanoate;
trans-4-(4-[(trans-4-[(R)-2-fluorodecanoyloxy]cyclohexyl)methoxy]phenyl)cyclohexyl (R)-2-fluorodecanoate;
trans-4-(2-[4-(trans-4-[(S)-2-fluoropropanoyloxy]cyclohexyl)phenyl]ethyl)cyclohexyl (S)-2-fluoropropanoate;
trans-4-(2-[4-(trans-4-[(S)-2-fluorobutanoyloxy]cyclohexyl)phenyl]ethyl)cyclohexyl (S)-2-fluorobutanoate;
trans-4-(2-[4-(trans-4-[(S)-2-fluoropentanoyloxy]cyclohexyl)phenyl]ethyl)cyclohexyl (S)-2-fluoropentanoate;
trans-4-(2-[4-(trans-4-[(S)-2-fluorohexanoyloxy]cyclohexyl)phenyl]ethyl)cyclohexyl (S)-2-fluorohexanoate;
trans-4-(2-[4-(trans-4-[(S)-2-fluoroheptanoyloxy]cyclohexyl)phenyl]ethyl)cyclohexyl (S)-2-fluoroheptanoate;
trans-4-(2-[4-(trans-4-[(S)-2-fluorooctanoyloxy]cyclohexyl)phenyl]ethyl)cyclohexyl (S)-2-fluorooctanoate;
trans-4-(2-[4-(trans-4-[(S)-2-fluorononanoyloxy]cyclohexyl)phenyl]ethyl)cyclohexyl (S)-2-fluorononanoate;
trans-4-(2-[4-(trans-4-[(S)-2-fluorodecanoyloxy]cyclohexyl)phenyl]ethyl)cyclohexyl (S)-2-fluorodecanoate;
trans-4, trans-4'-di[(S)-2-fluoropropanoyloxy]bicyclohexyl;
trans-4, trans-4'-di[(S)-2-fluorobutanoyloxy]bicyclohexyl;
trans 4, trans 4'-di[(S)-2-fluoropentanoyloxy]bicyclohexyl;
trans-4, trans-4'-di[(S)-2-fluorohexanoyloxy]bicyclohexyl, m.p. (C-I) 38.1° C., transition (S-S) 18.8° C., cl.p. (S-1) 22.3° C.;
trans 4, trans-4'-di[(S)-2-fluoroheptanoyloxy]bicylohexyl;
trans-4, trans-4'-di[(S)-2-fluorooctanoyloxy]bicyclohexyl;
trans-4, trans-4'-di[(S)-2-fluorononanoyloxy]bicyclohexyl;
trans-4, trans-4'-di[(S)-2-fluorodecanoyloxy]bicyclohexyl;
trans-4, trans-4'-di[(R)-2-fluoropropanoyloxy]bicyclohexyl;
trans-4, trans-4'-di[(R)-2-fluorobutanoyloxy]bicyclohexyl;
trans-4, trans-4'-di[(R)-2-fluoropentanoyloxy]bicyclohexyl;
trans-4, trans-4'-di[(R)-2-fluorohexanoyloxy]bicyclohexyl;
trans-4, trans-4'-di[(R)-2-fluoroheptanoyloxy]bicyclohexyl;
trans-4, trans-4'-di[(R)-2-fluorooctanoyloxy]bicyclohexyl;
trans-4, trans-4'-di[(R)-2-fluorononanoyloxy]bicyclohexyl;
trans-4, trans-4'-di[(R)-2-fluorodecanoyloxy]bicyclohexyl;
1,4-bis(trans-4-[(S)-2-fluoropropanoyloxy]cyclohexyl)-benzene;
1,4-bis(trans-4-[(S)-2-fluorobutanoyloxy]cyclohexyl)-benzene;
1,4-bis(trans 4-[(S).2-fluoropentanoyloxy]cyclohexyl)-benzene;
1,4-bis(trans-4-[(S)-2-fluorohexanoyloxy]cyclohexyl)-benzene;
1,4-bis(trans-4-[(S)-2-fluoroheptanoyloxy]cyclohexyl)-benzene;
1,4-bis(trans 4-[(S)-2-fluorooctanoyloxy]cyclohexyl)-benzene;
1,4-bis(trans-4-[(S)-2-fluorononanoyloxy]cyclohexyl)-benzene;

1,4-bis(trans 4-[(S)-2-fluorodecanoyloxy]cyclohexyl)benzene;
2-fluoro-1,4-bis(trans 4-[(S)-2-fluoropropanoyloxy]cyclohexyl)benzene;
2-fluoro-1,4-bis(trans-4-[(S)-2-fluoropropanoyloxy]cyclohexyl)benzene;
2-fluoro-1,4-bis(trans-4-[(S)-2-fluoropentanoyloxy]cyclohexyl)benzene;
2-fluoro 1,4-bis(trans-4-[(S)-2-fluorohexanoyloxy]cyclohexyl)benzene;
2-fluoro-1,4-bis(trans-4-[(S)-2-fluoroheptanoyloxy]cyclohexyl)benzene;
2-fluoro-1,4-bis(trans-4-[(S)-2-fluorooctanoyloxy]cyclohexyl)benzene;
2-fluoro 1,4-bis(trans-4-[(S)-2-fluorononanoyloxy]cyclohexyl)benzene;
2-fluoro-1,4-bis(trans-4-[(S)-2-fluorodecanoyloxy]cyclohexyl)benzene;
2-chloro-1,4-bis(trans-4-[(S)-2-fluoropropanoyloxy]cyclohexyl)benzene;
2-chloro-1,4-bis(trans-4-[(S)-2-fluorobutanoyloxy]cyclohexyl)benzene;
2-chloro-1,4-bis(trans-4-[(S)-2-fluoropentanoyloxy]cyclohexyl)benzene;
2-chloro-1,4-bis(trans-4-[(S)-2-fluorohexanoyloxy]cyclohexyl)benzene;
2-chloro-1,4-bis(trans-4-[(S)-2-fluoroheptanoyloxy]cyclohexyl)benzene;
2-chloro-1,4-bis(trans-4-[(S)-2-fluorooctanoyloxy]cyclohexyl)benzene;
2-chloro-1,4-bis(trans-4-[(S)-2-fluorononanoyloxy]cyclohexyl)benzene;
2-chloro-1,4-bis(trans-4-[(S)-2-fluorodecanoyloxy]cyclohexyl)benzene;
2-bromo-1,4-bis(trans-4-[(S)-2-fluoropropanoyloxy]cyclohexyl)benzene;
2-bromo-1,4-bis(trans-4-[(S)-2-fluorobutanoyloxy]cyclohexyl)benzene;
2-bromo-1,4-bis(trans-4-[(S)-2-fluoropentanoyloxy]cyclohexyl)benzene;
2-bromo-1,4-bis(trans-4-[(S)-2-fluorohexanoyloxy]cyclohexyl)benzene;
2-bromo-1,4-bis(trans-4-[(S)-2-fluoroheptanoyloxy]cyclohexyl)benzene;
2-bromo-1,4-bis(trans-4-[(S)-2-fluorooctanoyloxy]cyclohexyl)benzene;
2-bromo-1,4-bis(trans-4-[(S)-2-fluorononanoyloxy]cyclohexyl)benzene;
2-bromo-1,4-bis(trans 4-[(S)-2-fluorodecanoyloxy]cyclohexyl)benzene;
2-cyano-1,4-bis(trans-4-[(S)-2-fluoropropanoyloxy]cyclohexyl)benzene;
2-cyano-1,4-bis(trans-4-[(S)-2-fluorobutanoyloxy]cyclohexyl)benzene;
2-cyano-1,4-bis(trans-4-[(S)-2-fluoropentanoyloxy]cyclohexyl)benzene;
2-cyano-1,4-bis(trans-4-[(S)-2-fluorohexanoyloxy]cyclohexyl)benzene;
2-cyano-1,4-bis(trans 4-[(S)-2-fluoroheptanoyloxy]cyclohexyl)benzene;
2-cyano-1,4-bis(trans-4-[(S)-2-fluorooctanoyloxy]cyclohexyl)benzene;
2-cyano-1,4-bis(trans 4-[(S)-2-fluorononanoyloxy]cyclohexyl)benzene;
2-cyano-1,4-bis(trans-4-[(S)-2-fluorodecanoyloxy]cyclohexyl)benzene;
1,4-bis(trans-4-[(R)-2-fluoropropanoyloxy]cyclohexyl)benzene;
1,4-bis(trans-4-[(R)-2-fluorobutanoyloxy]cyclohexyl)benzene;
1,4-bis(trans-4-[(R)-2-fluoropentanoyloxy]cyclohexyl)benzene;
1,4-bis(trans-4-[(R)-2-fluorohexanoyloxy]cyclohexyl)benzene;
1,4-bis(trans-4-[(R)-2-fluoroheptanoyloxy]cyclohexyl)benzene;
1,4-bis(trans-4-[(R)-2-fluorooctanoyloxy]cyclohexyl)benzene;
1,4-bis(trans-4-[(R)-2-fluorononanoyloxy]cyclohexyl)benzene;
1,4-bis(trans-4-[(H)-2-fluorodecanoyloxy]cyclohexyl)benzene;
1,4-bis[(trans-4-[(S)-2-fluoropropanoyloxy]cyclohexyl)methoxy]benzene;
1,4-bis[(trans-4-[(S)-2-fluorobutanoyloxy]cyclohexyl)methoxy]benzene;
1,4-bis[(trans-4-[(S)-2-fluoropentanoyloxy]cyclohexyl)methoxy]benzene;
1,4-bis[(trans-4-[(S)-2-fluorohexanoyloxy]cyclohexyl)methoxy)benzene;
1,4-bis[(trans-4-[(S)-2-fluoroheptanoyloxy]cyclohexyl)methoxy]benzene;
1,4-bis[(trans-4-[(S)-2-fluorooctanoyloxy]cyclohexyl)methoxy]benzene;
1,4-bis[(trans-4-[(S)-2-fluorononanoyloxy]cyclohexyl)methoxy]benzene;
1,4-bis[(trans 4-[(S)-2-fluorodecanoyloxy]cyclohexyl)methoxy]benzene;
1,4-bis[(trans-4-[(R)-2-fluoropropanoyloxy]cyclohexyl)methoxy]benzene;
1,4-bis[(trans 4 [(R)-2-fluorobutanoyloxy]cyclohexyl)methoxy]benzene;
1,4-bis[(trans-4-[(R)-2-fluoropentanoyloxy]cyclohexyl)methoxy]benzene;
1,4-bis[(trans 4-[(R)-2-fluorohexanoyloxy]cyclohexyl)methoxy]benzene;
1 4-bis[(trans-4-[(R)-2-fluoroheptanoyloxy]cyclohexyl)methoxy]benzene;
1,4-bis[(trans 4-[(R)-2-fluorooctanoyloxy]cyclohexyl)methoxy]benzene;
1,4-bis[(trans-4-[(R)-2-fluorononanoyloxy]cyclohexyl)methoxy]benzene;
1,4-bis[(trans-4-[(R)-2-fluorodecanoyloxy]cyclohexyl)methoxy]benzene;
2-fluoro-1,4-bis[(trans-4-[(S)-2-fluorohexanoyloxy]cyclohexyl)methoxy]benzene;
2-chloro-1,4-bis[(trans-4-[(S)-2-fluorohexanoyloxy]cyclohexyl)methoxy]benzene;
2-bromo-1,4-bis[(trans-4-[(S)-2 fluorohexanoyloxy]cyclohexyl)methoxy]benzene;
2-cyano-1,4-bis[(trans-4-[(S)-2-fluorohexanoyloxy]cyclohexyl)methoxy]benzene;
1,4-bis[2-(trans-4-[(S)-2-fluoropropanoyloxy]cyclohexyl)ethyl]benzene;
1,4-bis[2-(trans-4-[(S)-2-fluorobutanoyloxy]cyclohexyl)ethyl]benzene;
1,4-bis[2-(trans-4-[(S)-2-fluoropentanoyloxy]cyclohexyl)ethyl]benzene;
1,4-bis[2-(trans-4-[(S)-2-fluorohexanoyloxy]cyclohexyl)ethyl]benzene;
1,4-bis[2-(trans-4-[(S)-2-fluoroheptanoyloxy]cyclohexyl)ethyl]benzene;
1,4-bis[2-(trans-4-[(S)-2-fluorooctanoyloxy]cyclohexyl)ethyl]benzene;
1,4-bis[2-(trans-4-[(S)-2-fluorononanoyloxy]cyclohexyl)ethyl]benzene;

1,4-bis[2-(trans-4-[(S)-2-fluorodecanoyloxy]cyclohexyl)ethyl]benzene;
1,4-bis[2-(trans-4-[(R)-2-fluoropropanoyloxy]cyclohexyl)ethyl]benzene;
1,4-bis[2-(trans-4-[(R)-2-fluorobutanoyloxy]cyclohexyl)ethyl]benzene;
1,4-bis[2-(trans-4-[(R).2-fluoropentanoyloxy]cyclohexyl)ethyl]benzene;
1,4-bis[2-(trans-4-[(R)-2-fluorohexanoyloxy]cyclohexyl)ethyl]benzene;
1,4-bis[2-(trans-4-[(R) 2-fluoroheptanoyloxy]cyclohexyl)ethyl]benzene;
1,4-bis[2-(trans-4-[(R)-2-fluorooctanoyloxy]cyclohexyl)ethyl]benzene;
1,4-bis[2-(trans-4-[(R)-2-fluorononanoyloxy]cyclohexyl)ethyl]benzene;
1,4-bis[2-(trans-4-[(R)-2-fluorodecanoyloxy]cyclohexyl)ethyl]benzene;
trans-4-(4-[(trans-4-[(2S,3S)-2-fluoro-3-methylpentanoyloxy]cyclohexyl)methoxy]phenyl)cyclohexyl (2S,3S)-2-fluoro-3-methylpentanoate;
trans-4-(2-[4-(trans-4-[(2S,3S)-2-fluoro-3-methylpentanoyloxy]cyclohexyl)phenyl]ethyl)cyclohexyl (2S,3S)-2-fluoro-3-methylpentanoate;
trans-4, trans-4'-di[(2S,3S)-2-fluoro-3-methylpentanoyloxy]bicyclohexyl;
1,4-bis(trans-4-[(2S,3S)-2-fluoro-3-methylpentanoyloxy]cyclohexyl)benzene;
1,4-bis[(trans-4-[(2S,3S)-2-fluoro-3-methylpentanoyloxy]cyclohexyl)methoxy]benzene;
1,4-bis[2-(trans-4-[(2S,3S)-2-fluoro-3-methylpentanoyloxy]cyclohexyl)ethyl]benzene.

EXAMPLE 5

0.2 g of (S)-2-fluorohexanoic acid (S-α-fluorocaproic acid), 0.7 g of trans-4-(4'-[(R)-2-octyl]oxycarbonyl-4-biphenylyl)cyclohexanol, 0.45 g of N,N'-dicyclohexylcarbodiimide, 3 mg of 4-(dimethylamino)pyridine and 30 ml of dichloromethane were reacted in an analogous manner to Example 1. This gave 0.5 g of trans 4-(4'-[(R)-2-octyl]oxycarbonyl-4-biphenylyl)cyclohexyl (S)-2-fluorohexanoate; m.p. (C-$S_A$) 34° C. cl.p. ($S_A$-I) 41° C.

The trans-4-(4'-[(R)-2-octyl]oxycarbonyl-4-biphenylyl)cyclohexanol used as the starting material was prepared as follows:

(a) A mixture of 20 g of 4-(4'amido-4-biphenylyl)cyclohexanone, 200 ml of 50% sulfuric acid and 400 ml of acetic acid was heated to a temperature of 115° C. overnight. The cooled reaction mixture was poured on to ice-water and the white precipitate was filtered off. The filter residue was washed with water and subsequently recrystallized from ethanol. This gave 9.9 g of 4-(4'-carboxy-4-biphenylyl)cyclohexanone.

(b) A mixture of 2 g of 4-(4'-carboxy-4-biphenylyl)cyclohexanone, 0.9 g of R-(−)-2-octanol, 2.0 g of N,N'-dicyclohexylcarbodiimide, 1 mg of 4-(dimethylamino)pyridine and 80 ml of dichloromethane was reacted in an analogous manner to Example 1. The residue was purified by chromatography on silica gel with hexane/ethyl acetate (vol. 7:3). This gave 1.5 g of 4-(4'-[(R)-2-octyl]oxycarbonyl-4biphenylyl)cyclohexanone.

(c) A suspension of 0.14 g of sodium borohydride in 10 ml of 1,2-dimethoxyethane was treated at 0° C. with a solution of 4-(4'-[(R)-2-octyl]oxycarbonyl-4-biphenylyl)cyclohexanone in 10 ml of 1,2-dimethoxyethane. The reaction mixture was stirred at room temperature for a further 30 minutes and then treated with 25% hydrochloric acid. The reaction mixture was extracted three times with 50 ml of diethyl ether each time. The combined organic phases were washed with sodium hydrogen carbonate solution and several times with water and subsequently dried over magnesium sulfate, filtered and concentrated. The residue was recrystallized twice from hexane and gave 0.8 g of trans-4-(4'-[(R)-2-octyl]oxycarbonyl 4-biphenylyl)cyclohexanol.

The following compounds can be prepared in an analogous manner:
trans 4-(4'-[(R)-2-Octyl]oxycarbonyl-4-biphenylyl)cyclohexyl (S)-2-fluoropropanoate;
trans-4-(4'-[(R)-2-octyl]oxycarbonyl-4-biphenylyl)cyclohexyl (S)-2-fluorobutanoate;
trans-4-(4'-[(R)-2-octyl]oxycarbonyl-4-biphenylyl)cyclohexyl (S)-2-fluoropentanoate;
trans-4-(4'-[(R)-2-octyl]oxycarbonyl-4-biphenylyl)cyclohexyl (S)-2-fluoroheptanoate;
trans-4-(4'-[(R)-2-octyl]oxycarbonyl-4-biphenylyl)cyclohexyl (S)-2-fluorooctanoate;
trans-4-(4'-[(R)-2-octyl]oxycarbonyl-4-biphenylyl)cyclohexyl (S)-2-fluorononanoate;
trans-4-(4'-[(R)-2-octyl]oxycarbonyl-4-biphenylyl)cyclohexyl (S)-2-fluorodecanoate;
trans-4-[2-(4'-[(R)-2-octyoxycarbonyl-4-biphenylyl)ethyl]cyclohexyl (S)-2-fluoropropanoate;
trans-4-[2-(4'-[(R)-2-octyl]oxycarbonyl-4-biphenylyl)ethyl]cyclohexyl (S)-2-fluorobutanoate;
trans-4-[2-(4'-[(R)-2-octyl]oxycarbonyl-4-biphenylyl)ethyl]cyclohexyl (S)-2-fluoropentanoate;
trans 4-[2-(4'-[(R)-2-octyl]oxycarbonyl- 4-biphenylyl)ethyl]cyclohexyl (S)-2-fluorohexanoate;
trans-4-[2-(4'-[(R)-2-octyl]oxycarbonyl-4-biphenylyl)ethyl]cyclohexyl (S)-2-fluoroheptanoate;
trans-4-[2-(4'-[(R)-2-octyl]oxycarbonyl-4-biphenylyl)ethyl]cyclohexyl (S)-2-fluorooctanoate;
trans-4-[2-(4'-[(R)-2-octyl]oxycarbonyl-4-biphenylyl)ethyl]cyclohexyl (S)-2-fluorononanoate;
trans-4-[2-(4'-[(R)-2-octyl]oxycarbonyl-4-biphenylyl)ethyl]cyclohexyl (S)-2-fluorodecanoate.

EXAMPLE 6

The use of the compounds of formula I in tilted smectic phases is illustrated by the mixtures set forth in Table I and by Mixture M-3. Percentages are wt. % of the respective components in the total mixture. The optically active doping substances of formula I which are denoted by D and the additional components denoted by C are the following compounds:
C-1=4-dodecyloxy-2-fluorobenzoic acid 4-[2-(trans-4-pentylcyclohexyl)ethyl]phenyl ester,
C-2=4-dodecyloxy-2-fluorobenzoic acid 4-[(trans-4-pentylcyclohexyl)methoxy]phenyl ester,
C-3=4-dodecyloxybenzoic acid 4-[2-(trans-4pentylcyclohexyl)ethyl]phenyl ester,
C-4=4-decyloxybenzoic acid 4-[2-(trans-4pentylcyclohexyl)ethyl]phenyl ester,
C-5=4-undecyloxybenzoic acid 4-[2-(trans-4pentylcyclohexyl)ethyl]phenyl ester,
C-6=2-(4-hexyloxyphenyl)-5-nonylpyrimidine,
C-7=2-(4-nonyloxyphenyl)-5-nonylpyrimidine,
C-8=2-(4-nonyloxyphenyl)-5-heptylpyrimidine,
C-9=2-(4-octyloxyphenyl)-5-heptylpyrimidine,
C-10=2-(4-heptyloxyphenyl)-5-heptylpyrimidine,
C-11=2-(4-hexyloxyphenyl)-5-heptylpyrimidine, C-12 = 2-(4-decyloxyphenyl)-5-decylpyrimidine,
C-13 = 2-(4-hexyloxyphenyl)-5-decylpyrimidine,
D-1 = trans-4-(4'-decyl-4-biphenylyl)cyclohexyl (S)-2-fluorohexanoate,
D-2 = trans 4-(4-[(trans-4-[(S) 2 fluorohexanoyloxy]cyclohexyl)methoxy]phenyl)cyclohexyl (S)-2-fluorohexanoate.

TABLE 1

|      | M-1    | M-2    |
|------|--------|--------|
| C-1  | 16.32% | 14.44% |
| C-2  | 4.57%  | 5.42%  |
| C-3  | 5.86%  | 5.23%  |
| C-4  | 5.25%  | 5.23%  |
| C-5  | 3.30%  | 4.87%  |
| C-6  | 12.11% | 12.09% |
| C-7  | 21.79% | 20.58% |
| C-8  | 2.78%  | 2.53%  |
| C-9  | 7.59%  | 6.23%  |
| C-10 | 4.92%  | 5.60%  |
| C-11 | —      | 4.51%  |
| C-12 | 3.58%  | —      |
| C-13 | 3.63%  | 3.52%  |
| D-1  | 8.30%  | —      |
| D-2  | —      | 9.75%  |

The melting points of the mixtures are difficult to determine. Crystallization or highly ordered smectic phases could not, however, be observed upon cooling to just below 0° C. The mixtures in accordance with Table 1 have the following properties:

Mixture M-1

M.p. <0° C., transitions $S_C^*$-$S_A$ 46.8° C., $S_A$-Ch 72.1° C., cl.p. (Ch-I) 89.2%.

Mixture M-2

M.p. <0° C., transitions $S_C^*$-$S_A$ 18.3° C., $S_A$-Ch 70.7° C., cl.p. (Ch-I) 86.1° C.

Mixture M-3

3.53 wt. % trans-5-hexyl-2-(4'octyloxy-4-biphenylyl)-1,3-dioxane,
3.53 wt. % trans-5-heptyl-2-(4'-heptyloxy-4-biphenylyl)-1,3-dioxane,
8.25 wt. % trans-5-heptyl-2-(4'-octyloxy-4-biphenylyl)-1,3-dioxane,
8.20 wt. % trans-5-nonyl-2-(4'-octyloxy-4-biphenylyl)-1,3-dioxane,
5.99 wt % 2-(4-hexyloxyphenyl)-5-octylpyrimidine,
12.73 wt. % 2-(4-hexyloxyphenyl)-5-nonylpyrimidine,
7.72 wt. % 2-(4-octyloxyphenyl)-5-heptylpyrimidine,
4.22 wt. % 2-(4-nonyloxyphenyl)-5-heptylpyrimidine,
5.89 wt. % 2-(4-nonyloxyphenyl)-5-octylpyrimidine,
25.44 wt. % 2-(4-nonyloxyphenyl)-5-nonylpyrimidine,
5.00 wt. % trans-4-(4 -decyl-4-biphenylyl)cyclohexyl (S)-2-fluorohexanoate,
9.50 wt. % trans-4-[4-(2,3-difluoro-4-dodecyloxybenzoyloxy) phenyl]cyclohexyl (S)-2-fluorohexanoate,
m.p. <0° C., transitions $S_C^*$-$S_A$ 61.1° C., $S_A$-Ch 83.7° C.; cl.p. (Ch-I) 94.7° C., pitch 9 μm. The mixture had a response time of 90 μs at 25° C. in a cell according to Appl. Phys. 36, 899 (1980) utilizing a plate separation of 2 μm and a potential of 20 V (square wave, peak to peak).

We claim:

1. An optically active compound of formula

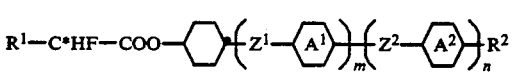

wherein m stands for the number 1 and $R^2$ is alkyl, alkenyl, alkoxy, alkenyloxy, haloalkyl, alkoxycarbonyl or haloalkanoyloxy with up to 15 carbon atoms; $R^1$ is alkyl, alkenyl, alkoxy alkyl or alkenyloxy alkyl with up to 15 carbon atoms; $Z^1$ and $Z^2$ each independently are a single covalent bond, —CH$_2$O—, —OCH$_2$—, —CH$_2$CH$_2$—, —COO—, or —OOC—; n stands for the number 0 or 1; rings $A^1$ and $A^2$ each independently are 1,4-phenylene unsubstituted or substituted with at least one of halogen, cyano or methyl, or ring $A^2$ is a pyrimidin-2,5-diyl or pyridin-2,5-diyl; and C* denotes a chiral carbon atom; provided that simultaneously $R^1$ is not an alkyl group, m and n are not the number 1, $Z^1$ is not the group, —CH$_2$CH$_2$— or —CH$_2$O— and ring $A^1$, $Z^2$, ring $A^2$ and $R^2$ together are not 4-(5-alkyl-2-pyrimidinyl)-phenyl.

2. A compound according to claim 1, wherein rings $A^1$ and $A^2$ each independently are 1,4-phenylene, fluoro-1,4-phenylene, chloro-1,4-phenylene, bromo-1,4-phenylene, cyano-1,4-phenylene, 2,3-difluoro-1,4-phenylene, or ring $A^2$ also is pyridine-2,5-diyl or pyrimidine-2,5-diyl.

3. A compound according to claim 1, of formulas

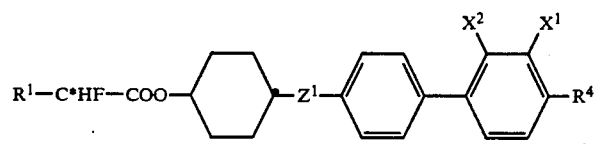

I-1

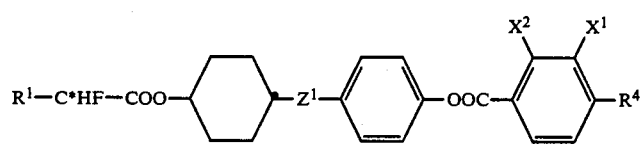

I-2

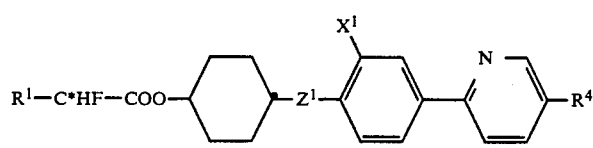

I-3

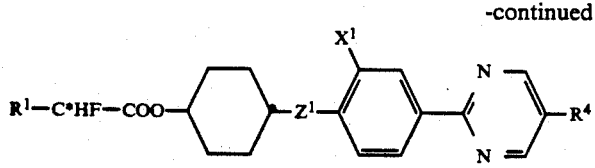

wherein $R^1$, $Z^1$, and $C^*$ have the significances of claim 1; $R^4$ is $R^2$ as defined in claim 1; $X^1$ and $X^2$ are hydrogen, fluorine, chlorine, bromine, cyano or methyl; provided that in the formulas I-4 $X^1$ is fluorine, chlorine, bromine, cyano or methyl when $Z^1$ is —CH$_2$CH$_2$— or —CH$_2$O.

4. A compound according to claim 1, wherein $Z^1$ is a single covalent bond, —CH$_2$O—, —CH$_2$CH$_2$— or —COO—.

5. A compound according to claim 1, wherein $R^1$ is $C_3$-$C_{15}$-alkyl.

6. A compound according to claim 1, wherein $R^2$ is a residue $R^4$ and $R^4$ is alkyl, alkenyl, alkoxy, alkenyloxy, haloalkoxy, alkoxycarbonyl or haloalkanoyloxy with up to 15 carbon atoms.

7. An optically active compound of formula

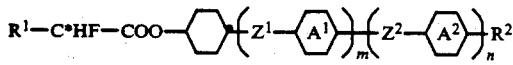 I wherein m stands for the number 1 and $R^2$ is alkyl, alkenyl, alkoxy, alkenyloxy, haloalkyl, alkoxycarbonyl or haloalkanoyloxy with up to 15 carbon atoms; $R^1$ is an alkyl, alkenyl, alkoxy alkyl or alkenyloxy alkyl with up to 15 carbon atoms; $Z^1$ and $Z^2$ each independently are a single covalent bond, —CH$_2$O—, —OCH$_2$—, —CH$_2$CH$_2$—, —COO—, or —OOC—; n stands for the number 0 or 1; rings $A^1$ and $A^2$ each independently are 1,4-phenylene unsubstituted or substituted with at least one of halogen, cyano or methyl, or ring $A^2$ is a pyrimidin-2,5-diyl or pyridin-2,5-diyl; and $C^*$ denotes a chiral carbon atom; provided that simultaneously $R^1$ is not an alkyl group, m and n are not the number 1, $Z^1$ is not the group, —CH$_2$CH$_2$— or —CH$_2$O— and ring $A^1$, $Z^2$, ring $A^2$ and $R^2$ together are not 4-(5-alkyl-2-pyrimidinyl)-phenyl.

8. An electro-optical cell comprising:
a) two plate means;
b) a liquid crystal means disposed between two plate means and including a compound of formula

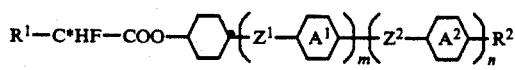 I wherein m stands for the number 1 and $R^2$ is alkyl, alkenyl, alkoxy, alkenyloxy, haloalkyl, alkoxycarbonyl or haloalkanoyloxy with up to 15 carbon atoms; $R^1$ is an alkyl, alkenyl, alkoxy alkyl or alkenyloxy alkyl with up to 15 carbon atoms; $Z^1$ and $Z^2$ each independently are a single covalent bond, —CH$_2$O—, —OCH$_2$—, —CH$_2$CH$_2$—, —COO—, or —OOC—; n stands for the number 0 or 1; rings $A^1$ and $A^2$ each independently are 1,4-phenylene unsubstituted or substituted with at least one of halogen, cyano or methyl, or ring $A^2$ is a pyrimidin-2,5-diyl or pyridin-2,5-diyl; and $C^*$ denotes a chiral carbon atom; provided that simultaneously $R^1$ is not an alkyl group, m and n are not the number 1, $Z^1$ is not the group, —CH$_2$CH$_2$— or —CH$_2$O— and ring $A^1$, $Z^2$, ring $A^2$ and $R^2$ together are not 4-(5-alkyl-2-pyrimidinyl)-phenyl; and
c) means for applying an electrical potential to said plate means.

* * * * *